(12) United States Patent
Fujimagari et al.

(10) Patent No.: US 11,121,112 B2
(45) Date of Patent: Sep. 14, 2021

(54) SOLID-STATE IMAGE PICKUP ELEMENT WITH DAM TO CONTROL RESIN OUTFLOW

(71) Applicant: SONY SEMICONDUCTOR SOLUTIONS CORPORATION, Kanagawa (JP)

(72) Inventors: Junichiro Fujimagari, Kanagawa (JP); Tomohiro Ohkubo, Kumamoto (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 42 days.

(21) Appl. No.: 16/482,435

(22) PCT Filed: Feb. 19, 2018

(86) PCT No.: PCT/JP2018/005651
§ 371 (c)(1),
(2) Date: Jul. 31, 2019

(87) PCT Pub. No.: WO2018/159344
PCT Pub. Date: Sep. 7, 2018

(65) Prior Publication Data
US 2019/0385968 A1 Dec. 19, 2019

(30) Foreign Application Priority Data

Mar. 3, 2017 (JP) .............................. JP2017-040131

(51) Int. Cl.
*H01L 23/00* (2006.01)
*H01L 27/146* (2006.01)
(Continued)

(52) U.S. Cl.
CPC .............. *H01L 24/32* (2013.01); *H01L 24/16* (2013.01); *H01L 24/73* (2013.01); *H01L 24/81* (2013.01);
(Continued)

(58) Field of Classification Search
CPC ...................................................... H01L 24/32
(Continued)

(56) References Cited

U.S. PATENT DOCUMENTS

2010/0201834 A1* 8/2010 Maruyama ........ H01L 27/14636
348/222.1
2013/0264599 A1 10/2013 Kikuchi et al.
(Continued)

FOREIGN PATENT DOCUMENTS

CN 106796941 A 5/2017
CN 107078140 A 8/2017
(Continued)

OTHER PUBLICATIONS

International Search Report and Written Opinion of PCT Application No. PCT/JP2018/005651, dated Apr. 24, 2018, 10 pages of ISRWO.

*Primary Examiner* — Ajay Arora
(74) *Attorney, Agent, or Firm* — Chip Law Group

(57) ABSTRACT

The present technology relates to a solid-state image pickup element, electronic equipment, and a semiconductor apparatus that make it possible to reduce a surface reflection in an area in which a slit is formed and improve flare characteristics. A solid-state image pickup element includes a pixel area in which a plurality of pixels is two-dimensionally arranged in a matrix, a chip mounting area in which a chip is flip-chip mounted, and a dam area that is arranged around the chip mounting area and in which one or more slits that block an outflow of a resin are formed. In the dam area, the
(Continued)

same OCL as that in the pixel area is formed. The present technology can be applied to a solid-state image pickup element etc. in which a chip is flip-chip mounted, for example.

11 Claims, 15 Drawing Sheets

(51) Int. Cl.
*H04N 5/369* (2011.01)
*A61B 1/05* (2006.01)
*B60R 11/04* (2006.01)
*G05D 1/02* (2020.01)

(52) U.S. Cl.
CPC .............. *H01L 24/83* (2013.01); *H01L 24/92* (2013.01); *H01L 27/1462* (2013.01); *H01L 27/1469* (2013.01); *H01L 27/14618* (2013.01); *H01L 27/14623* (2013.01); *H01L 27/14634* (2013.01); *H01L 27/14643* (2013.01); *H01L 27/14685* (2013.01); *H04N 5/369* (2013.01); *A61B 1/05* (2013.01); *B60R 11/04* (2013.01); *G05D 1/0231* (2013.01); *H01L 2224/16147* (2013.01); *H01L 2224/26145* (2013.01); *H01L 2224/32145* (2013.01); *H01L 2224/73204* (2013.01); *H01L 2224/92125* (2013.01)

(58) Field of Classification Search
USPC .......................................................... 257/432
See application file for complete search history.

(56) References Cited

U.S. PATENT DOCUMENTS

| | | | |
|---|---|---|---|
| 2017/0256577 A1* | 9/2017 | Inoue | ..................... H04N 5/369 |
| 2017/0317127 A1 | 11/2017 | Hareyama | |

FOREIGN PATENT DOCUMENTS

| | | | |
|---|---|---|---|
| CN | 107112341 A | 8/2017 | |
| JP | 53-112061 A | 9/1978 | |
| JP | 2013-012518 A | 1/2013 | |
| JP | 2016-163011 A | 9/2016 | |
| KR | 10-2017-0057229 A | 5/2017 | |
| KR | 10-2017-0078627 A | 7/2017 | |
| KR | 10-2017-0124526 A | 11/2017 | |
| TW | 201611255 A | 3/2016 | |
| WO | 2012/093426 A1 | 7/2012 | |
| WO | 2016/039173 A1 | 3/2016 | |
| WO | 2016/072279 A1 | 5/2016 | |
| WO | 2016/139914 A1 | 9/2016 | |
| WO | WO-2016139914 A1 * | 9/2016 | ......... H01L 27/1469 |

\* cited by examiner

SOLID-STATE IMAGE PICKUP ELEMENT WITH DAM TO CONTROL RESIN OUTFLOW

CROSS REFERENCE TO RELATED APPLICATIONS

This application is a U.S. National Phase of International Patent Application No. PCT/JP2018/005651 filed on Feb. 19, 2018, which claims priority benefit of Japanese Patent Application No. JP2017-040131 filed in the Japan Patent Office on Mar. 3, 2017. Each of the above-referenced applications is hereby incorporated herein by reference in its entirety.

TECHNICAL FIELD

The present technology relates to a solid-state image pickup element, electronic equipment, and a semiconductor apparatus. More particularly, the present technology relates to a solid-state image pickup element, electronic equipment, and a semiconductor apparatus that make it possible to reduce a surface reflection in an area in which a slit is formed and improve flare characteristics.

BACKGROUND ART

When flip-chip mounting is performed on a substrate via a solder bump, a method for injecting a resin called an underfill resin between a substrate and a chip to be filled therewith and then curing the filled resin has been taken as means of improving connection reliability.

In PTL 1, the present applicant proposes a structure in which a slit (groove) that blocks an outflow of an underfill resin is formed around an area in which a chip is mounted on a substrate.

CITATION LIST

Patent Literature

[PTL 1]
WO 2016/039173

SUMMARY

Technical Problem

However, in a structure proposed in PTL 1, an area in which a slit is formed has a flat surface, and therefore, a surface reflection from the flat surface is strong, causing flare to be generated.

The present technology has been made in view of such a situation as described above, and it is an object of the present technology to make it possible to reduce a surface reflection in an area in which a slit is formed and improve flare characteristics.

Solution to Problem

A solid-state image pickup element according to a first aspect of the present technology includes a pixel area in which a plurality of pixels is two-dimensionally arranged in a matrix, a chip mounting area in which a chip is flip-chip mounted, and a dam area that is arranged around the chip mounting area and in which one or more slits that block an outflow of a resin are formed, in which in the dam area, the same OCL as that in the pixel area is formed.

Electronic equipment according to a second aspect of the present technology includes a solid-state image pickup element having a pixel area in which a plurality of pixels is two-dimensionally arranged in a matrix, a chip mounting area in which a chip is flip-chip mounted, and a dam area that is arranged around the chip mounting area and in which one or more slits that block an outflow of a resin are formed, and in the dam area, the same OCL as that in the pixel area is formed.

In the first and the second aspects of the present technology, a pixel area in which a plurality of pixels is two-dimensionally arranged in a matrix, a chip mounting area in which a chip is flip-chip mounted, and a dam area that is arranged around the chip mounting area and in which one or more slits that block an outflow of a resin are formed, are provided, in which, in the dam area, the same OCL as that in the pixel area is formed.

A semiconductor apparatus according to a third aspect of the present technology includes an OCL area in which an OCL is formed in a matrix, a chip mounting area in which a chip is flip-chip mounted, and a dam area that is arranged around the chip mounting area and in which one or more slits that block an outflow of a resin are formed, in which, in the dam area, the same OCL as that in the OCL area is formed.

In the third aspect of the present technology, there are provided an OCL area in which an OCL is formed in a matrix, a chip mounting area in which a chip is flip-chip mounted, and a dam area that is arranged around the chip mounting area and in which one or more slits that block an outflow of a resin are formed, in which, in the dam area, the same OCL as that in the OCL area is formed.

The solid-state image pickup element, the electronic equipment, and the semiconductor apparatus may be independent apparatuses or modules incorporated into other apparatuses.

Advantageous Effects of Invention

According to the first to the third aspects of the present technology, it is possible to reduce a surface reflection in an area in which a slit is formed and improve flare characteristics.

In addition, advantageous effects disclosed herein are not necessarily limited thereto and may be any effects disclosed in the present disclosure.

DESCRIPTION OF EMBODIMENTS

Hereinafter, modes for carrying out the present technology (hereinafter, referred to as embodiments) will be described. In addition, a description is made in the following order.
1. Plan View of Solid-State Image Pickup Element
2. Cross-Sectional View of First Embodiment
3. Cross-Sectional View of Second Embodiment
4. Variation Example
5. Manufacturing Method
6. Application Example to Electronic Equipment
7. Usage Example of Image Sensor
8. Application Example to In-Vivo Information Acquisition System
9. Application Example to Endoscopic Surgery System
10. Application Example to Mobile Body <1. Plan View of Solid-State Image Pickup Element>

Figure 1:
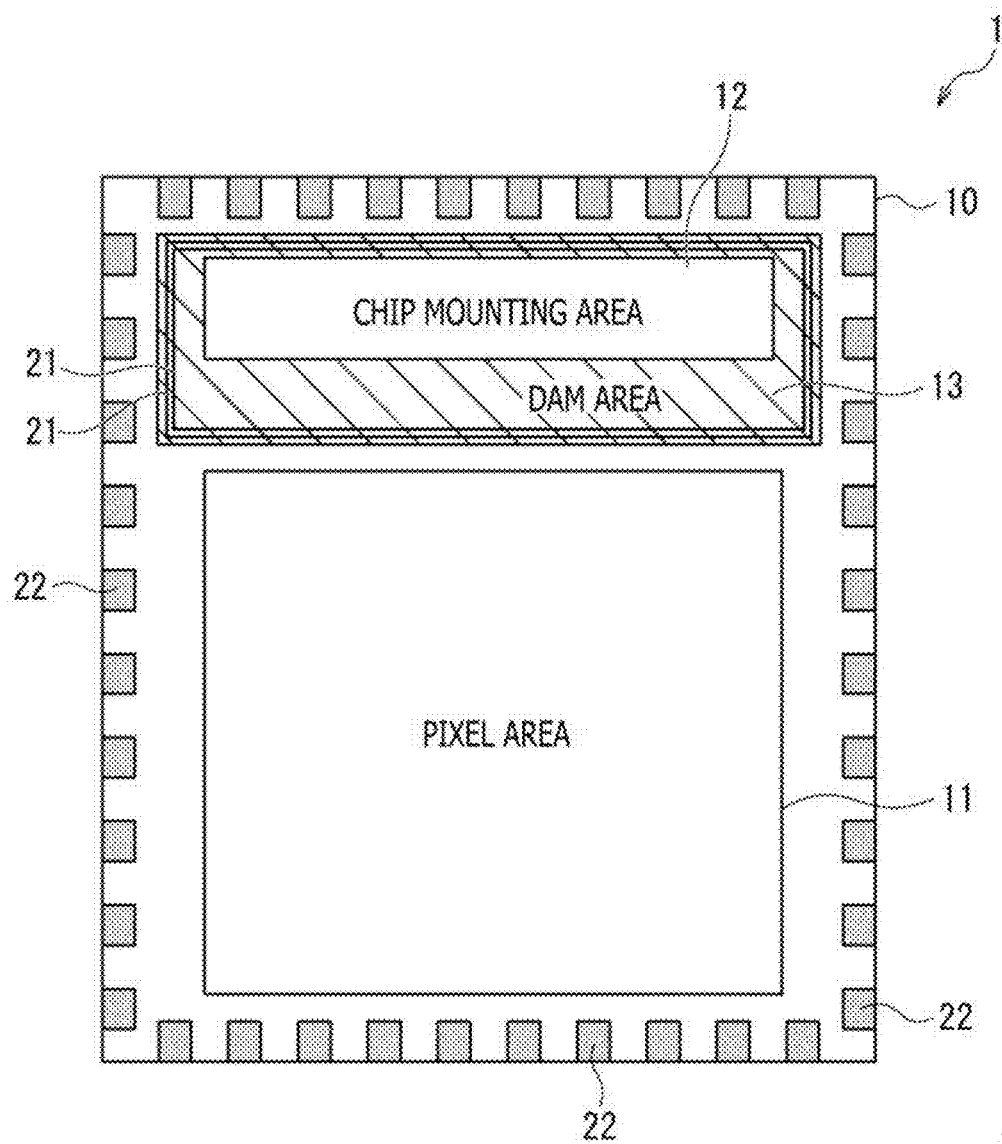
FIG. 1 is a plan view of a solid-state image pickup element to which the present technology is applied.

FIG. 1 is a plan view of a solid-state image pickup element to which the present technology is applied.

A solid-state image pickup element 1 depicted in FIG. 1 includes a pixel area 11 in which a plurality of pixels each having a photoelectric conversion unit that generates and accumulates an optical charge depending on an amount of received light is two-dimensionally arranged in a matrix in the row direction and in the column direction, a chip mounting area 12 in which a chip 61 (FIG. 2) in which a circuit for performing predetermined signal processing is formed is flip-chip mounted, and a dam area 13 that is arranged around the chip mounting area 12 on a semiconductor substrate 10 using silicon (Si), for example, as a semiconductor. An area depicted by oblique lines depicted in FIG. 1 is the dam area 13. In the dam area 13, a plurality of slits 21 that is grooves that block an outflow of a resin is formed (in an example depicted in FIG. 1, two slits 21 are formed). The slit 21 that blocks an outflow of the resin is also referred to as a dam.

A plurality of electrode pads 22 is formed at an outer peripheral part of the solid-state image pickup element 1. The electrode pad 22 is used for a contact of a probe or wire bonding in an inspection step.

<2. Cross-Sectional View of First Embodiment>

Figure 2:
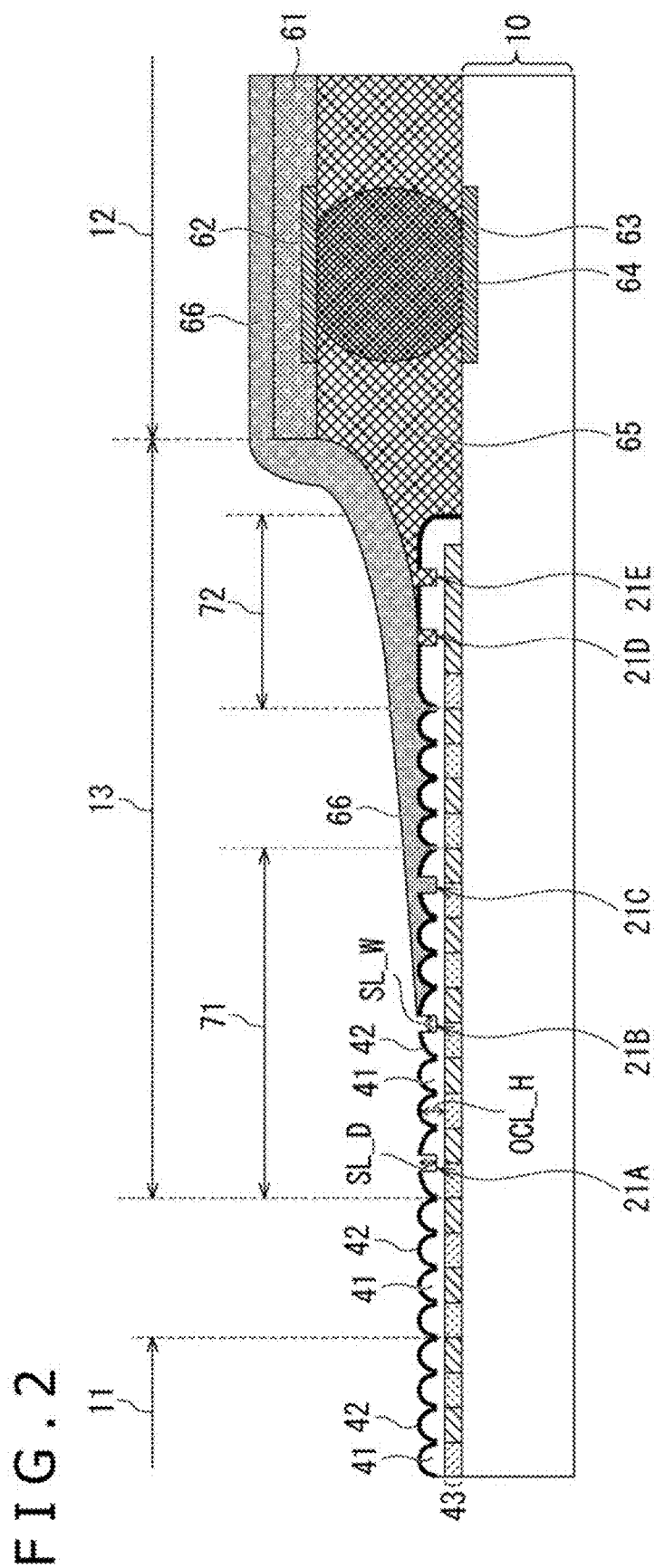
FIG. 2 is a cross-sectional view of the solid-state image pickup element according to a first embodiment.

FIG. 2 is a cross-sectional view of the solid-state image pickup element 1 according to a first embodiment.

FIG. 2 is a cross-sectional view including respective ends of the pixel area 11 and the chip mounting area 12, and the dam area 13 therebetween.

In the pixel area 11, a photodiode (not depicted) functioning as a photoelectric conversion unit is formed in a pixel unit within the semiconductor substrate 10. Also, an OCL (on chip lens) 41 is formed in the pixel unit on an upper side of the semiconductor substrate 10. Over an upper surface of the OCL 41, for example, an antireflection film (low reflection film) 42 using an LTO (Low Temperature Oxide) film is formed. In addition, a color filter layer 43 passing light of a predetermined wavelength such as R (red), G (green), or B (blue) is formed between the OCL 41 and the semiconductor substrate 10.

The OCL 41 is formed by silicon nitride (SiN), or a resin material such as a styrene resin, an acrylic resin, a styrene-acrylic copolymer resin, or a siloxane resin, for example. Further, the antireflection film 42 may be formed using a material such as silicon nitride (SiN), hafnium oxide ($HfO_2$), aluminum oxide ($Al_2O_3$), zirconium dioxide ($ZrO_2$), tantalum oxide ($Ta_2O_5$), titanium oxide ($TiO_2$), lanthanum oxide ($LA_2O_3$), praseodymium oxide ($Pr_2O_3$), cerium oxide ($CeO_2$), neodymium oxide ($Nd_2O_3$), promethium oxide ($Pm_2O_3$), samarium oxide ($Sm_2O_3$), europium oxide ($Eu_2O_3$), gadolinium oxide ($Gd_2O_3$), terbium oxide ($Tb_2O_3$), dysprosium oxide ($Dy_2O_3$), holmium oxide ($Ho_2O_3$), thulium oxide ($Tm_2O_3$), ytterbium oxide ($Yb_2O_3$), lutetium oxide ($Lu_2\ O_3$), yttrium oxide ($Y_2O_3$), or the like.

In the chip mounting area 12, the chip 61 is flip-chip mounted on the semiconductor substrate 10. Specifically, an electrode part 62 of the chip 61 and an electrode part 62 of the semiconductor substrate 10 are electrically connected via a solder bump 64.

Into a clearance other than the solder bump 64 between the chip 61 and the semiconductor substrate 10, an underfill resin 65 is filled. The underfill resin 65 includes, for example, a UV (ultraviolet) curable resin, a thermal curable resin, or the like. Further, the underfill resin 65 is injected into the clearance between the chip 61 and the semiconductor substrate 10 and then is cured.

An upper surface and side surfaces of the chip 61 and the underfill resin 65 around the chip 61 are covered with a light-shielding resin 66 including a black resin etc. having a light-shielding effect. The light-shielding resin 66 also includes a UV (ultraviolet) curable resin, a thermal curable resin, or the like. Further, the light-shielding resin 66 is coated by a dispenser and then is cured.

Meanwhile, the color filter layer 43 and OCLs 41 formed in the pixel area 11 are disposed in an extended manner and formed in the dam area 13. In an example depicted in FIG. 2, the pixel area 11 and the dam area 13 are separated from each other by a distance corresponding to four pixels. Further, the OCL 41, the antireflection film 42, and the color filter layer 43 are formed even in an area between the pixel area 11 and the dam area 13. The area between the pixel area 11 and the dam area 13 may be omitted or considered as a portion of the dam area 13.

A plurality of slits 21 is formed in the dam area 13. In FIG. 2, an example in which five slits 21A to 21E are formed in the dam area 13 is depicted; however, the number of the slits 21 is not particularly limited thereto when it is equal to or more than two.

In the example depicted in FIG. 2, three slits 21A to 21C close to the pixel area 11 are slits that block an outflow of the light-shielding resin 66 to the pixel area 11 and electrode pads 22. Further, two slits 21D and 21E close to the chip mounting area 12 are slits that block an outflow of the underfill resin 65 to the pixel area 11 and electrode pads 22. Accordingly, the dam area 13 at least includes a light-shielding resin dam area 71 in which the slits 21 that block an outflow of the light-shielding resin 66 to the pixel area 11 and electrode pads 22 are formed and a UF (underfill) dam area 72 in which the slits 21 that block an outflow of the underfill resin 65 to the pixel area 11 and electrode pads 22 are formed.

A width SL_W of the slit 21 is, for example, formed approximately in 2 to 10 μm. A depth SL_D of the slit 21 depends on a height OCL_H of the OCL 41. When the height OCL_H of the OCL 41 is set to approximately 1.5 to 3.0 μm, for example, the depth SL_D of the slit 21 requires approximately 1.0 μm.

The example depicted in FIG. 2 is an example in the case in which the slits 21 are manufactured by a manufacturing method for forming the slit 21 after the OCLs 41 and the antireflection films 42 are formed. Therefore, the antireflection film 42 is not formed on an inner peripheral surface of the slit 21. However, after the OCLs 41 and the slits 21 are formed, the antireflection films 42 may be formed. In the case, the antireflection film 42 can be formed also over the inner peripheral surface (side surfaces and a bottom surface) of the slit 21.

Figure 3:
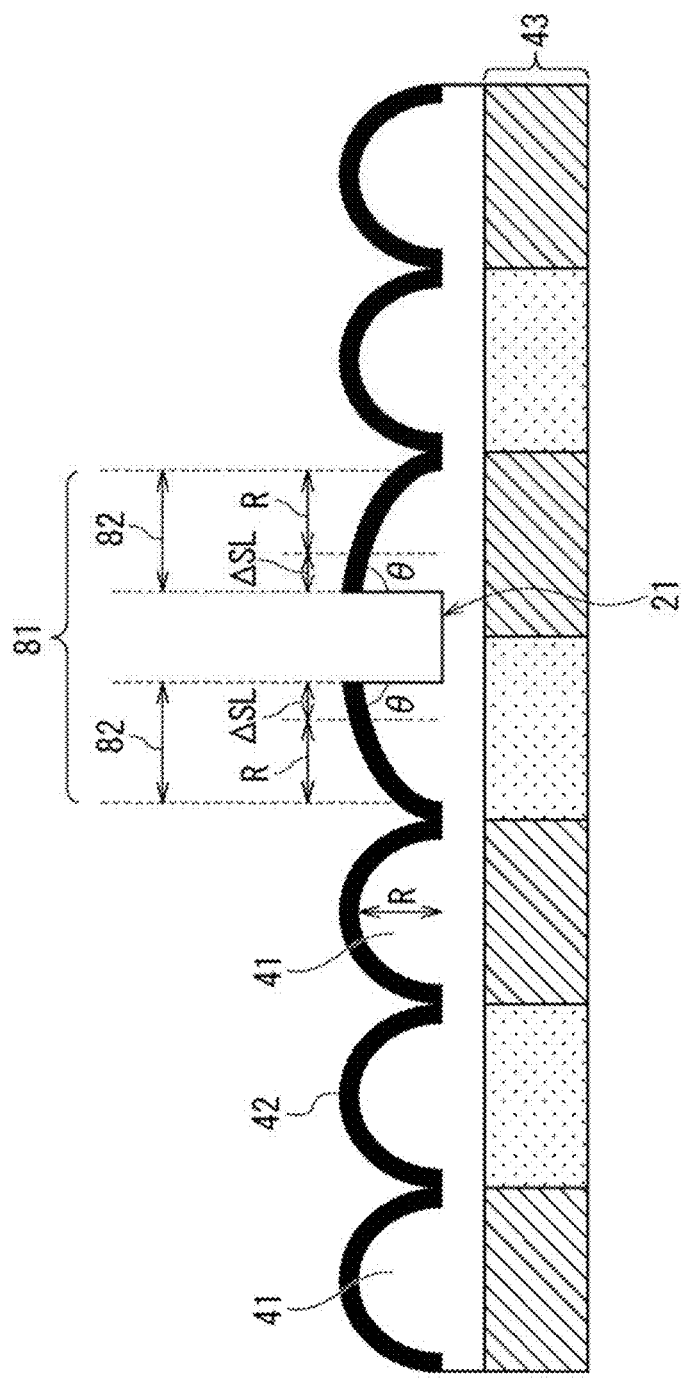
FIG. 3 is a cross-sectional view of a vicinity of a slit area depicted in FIG. 2.

As depicted in FIG. 3, a plane size of a slit area 81 that is an area in which the slit 21 is formed can be formed, for example, by a size corresponding to two pixels or three pixels of the pixel area 11, in other words, by a plane size that is an integral multiple of that of the OCL 41. Note that, as a matter of course, the plane size of the slit area 81 is not limited to an integral multiple of that of the OCL 41 but may be formed by an arbitrary size.

Further, as depicted in FIG. 3, the slit area 81 needs to be formed such that a distance 82 from an outer peripheral surface (each end surface) of the slit area 81 to the slit 21 is a distance equal to or more than a sum (R+ΔSL) of a radius R of the OCL 41 in the pixel area 11 and a formation position error ΔSL in a plane direction when the slit is formed. Thereby, an angle θ formed between a vertical plane of the slit 21 and a top portion of an OCL material becomes an angle close to 90 degrees. Therefore, a function of a dam that blocks the underfill resin 65 or the light-shielding resin 66 is enhanced. Note that, when the distance 82 is increased excessively, a flat area of the OCL material is enlarged, and therefore, optimization of process conditions and a layout is required.

In the foregoing description, as described with reference to FIGS. 2 and 3, according to the first embodiment, the OCLs similar to the OCLs 41 in the pixel area 11 are disposed in an extended manner and formed in the dam area 13 around the chip mounting area 12, and as a result a flat area is eliminated. Accordingly, a surface reflection can be reduced, and flare characteristics can be improved.

Further, an upper surface and side surfaces of the chip 61 that is flip-chip mounted and the underfill resin 65 are covered with the light-shielding resin 66. Therefore, the flare characteristics can be further improved.

A plurality of slits 21 that blocks an outflow of resins is formed in the dam area 13. Accordingly, the slits 21 can block an outflow of the underfill resin 65 and the light-shielding resin 66 to the pixel area 11 and electrode pads 22.

<3. Cross-Sectional View of Second Embodiment>

Figure 4:
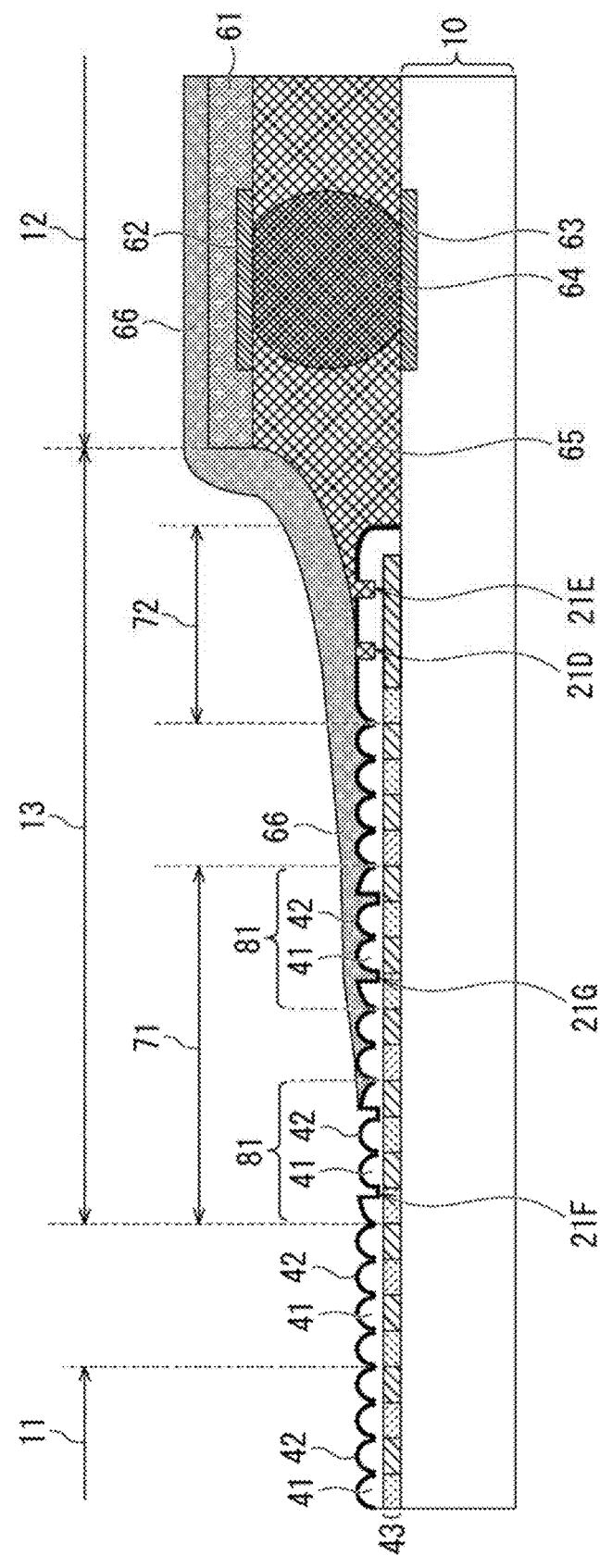
FIG. 4 is a cross-sectional view of the solid-state image pickup element according to a second embodiment.

FIG. 4 is a cross-sectional view according to a second embodiment of the solid-state image pickup element 1.

FIG. 4 is a view corresponding to the cross-sectional view depicted in FIG. 2 according to the first embodiment. Same reference symbols are given to components common to those in the first embodiment, and descriptions thereof are appropriately omitted.

In the second embodiment, the same OCLs 41 as the OCLs 41 in the pixel area 11 are formed, as a low reflection projection, on bottom surfaces of slits 21F and 21G that are formed in the slit areas 81 of the dam area 13. In an example depicted in FIG. 4, an example in which two OCLs 41 are formed on the bottom surfaces of the slits 21F and 21G is depicted. Further, the number of the OCLs 41 that are formed on the bottom surfaces of the slits 21F and 21G is arbitrary. In addition, the antireflection films 42 are also formed over the upper surfaces of the OCLs 41 that are formed on the bottom surfaces of the slits 21F and 21G.

Thus, one or more of the same OCLs as the OCLs 41 formed in the pixel area 11 can be formed, as the low reflection projection, on the bottom surfaces of the slits 21 that are formed in the dam area 13.

Alternatively, one or more OCLs different from the OCLs 41 that are formed in the pixel area 11, for example, OCLs having a size smaller than that of the OCL 41 may be formed.

Figure 5:
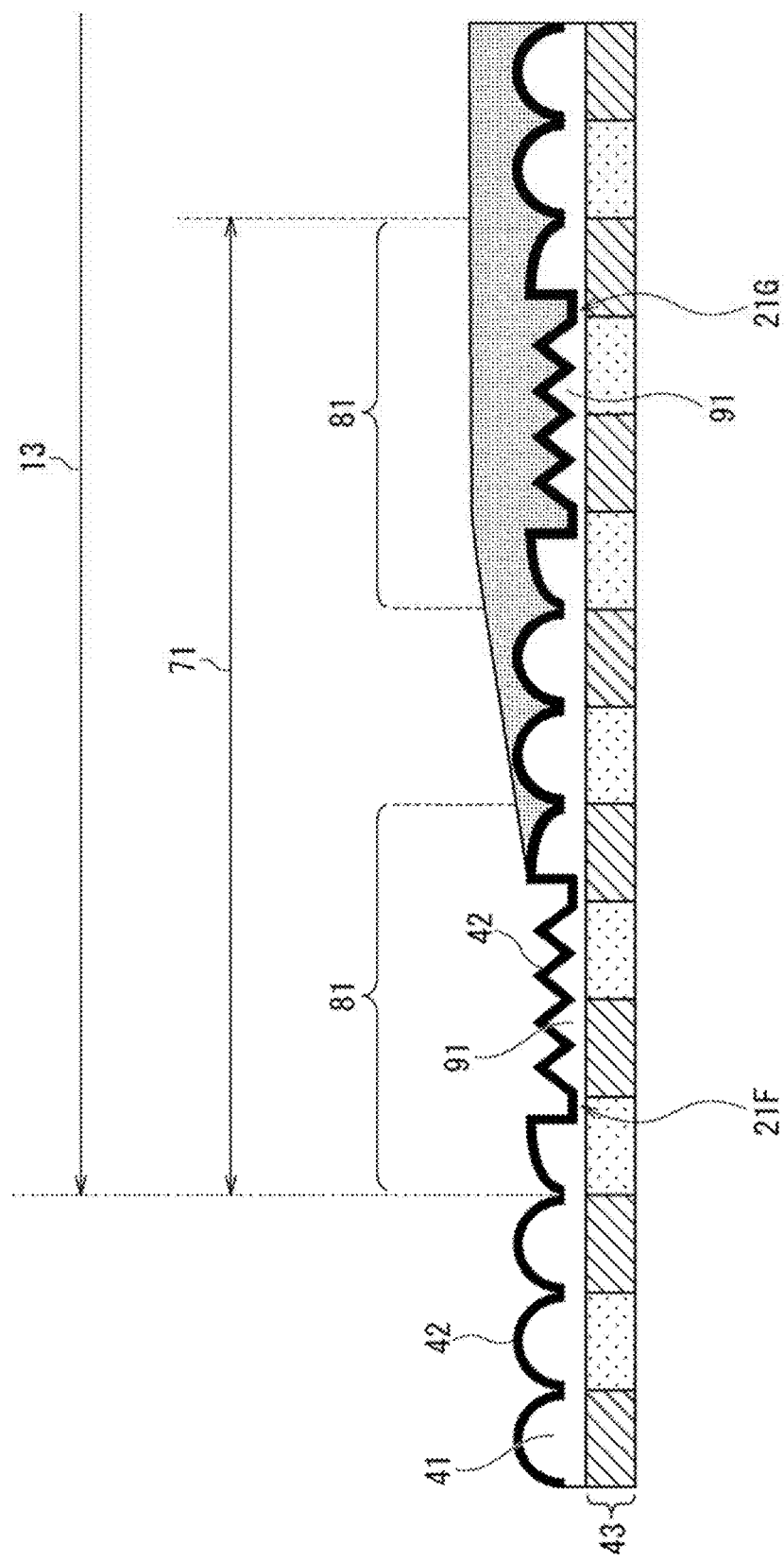
FIG. 5 is a cross-sectional view depicting an example of a low reflection projection that is formed on a bottom surface of a slit.

Alternatively, a low reflection projection 91 having a shape different from that of the OCL 41 that is formed in the pixel area 11, for example, the low reflection projection 91 having a shape of a triangular pyramid or a quadrangular pyramid as depicted in FIG. 5 may be formed. The antireflection film 42 is also formed over an upper surface of the low reflection projection 91.

As described above, according to the second embodiment, the OCLs 41 similar to those in the pixel area 11 are disposed in an extended manner and formed in the dam area 13 around the chip mounting area 12, and a flat area is eliminated. Accordingly, the surface reflection can be reduced and the flare characteristics can be improved.

In addition, the upper surface and side surfaces of the chip 61 and the underfill resin 65 are covered with the light-shielding resin 66, and therefore, the flare characteristics can be further improved.

A plurality of slits 21 that block an outflow of resins are formed in the dam area 13. Therefore, the outflow of the underfill resin 65 and the light-shielding resin 66 to the pixel area 11 and electrode pads 22 can be blocked.

Further, the same OCLs as the OCLs 41 in the pixel area 11, or the like, are formed as the low reflection projection on the bottom surfaces of one or more of the slits 21 that are formed in the dam area 13. Accordingly, the flare characteristics can be improved.

<4. Variation Example>

Variation examples of the first and the second embodiments will be described.

Figure 6:
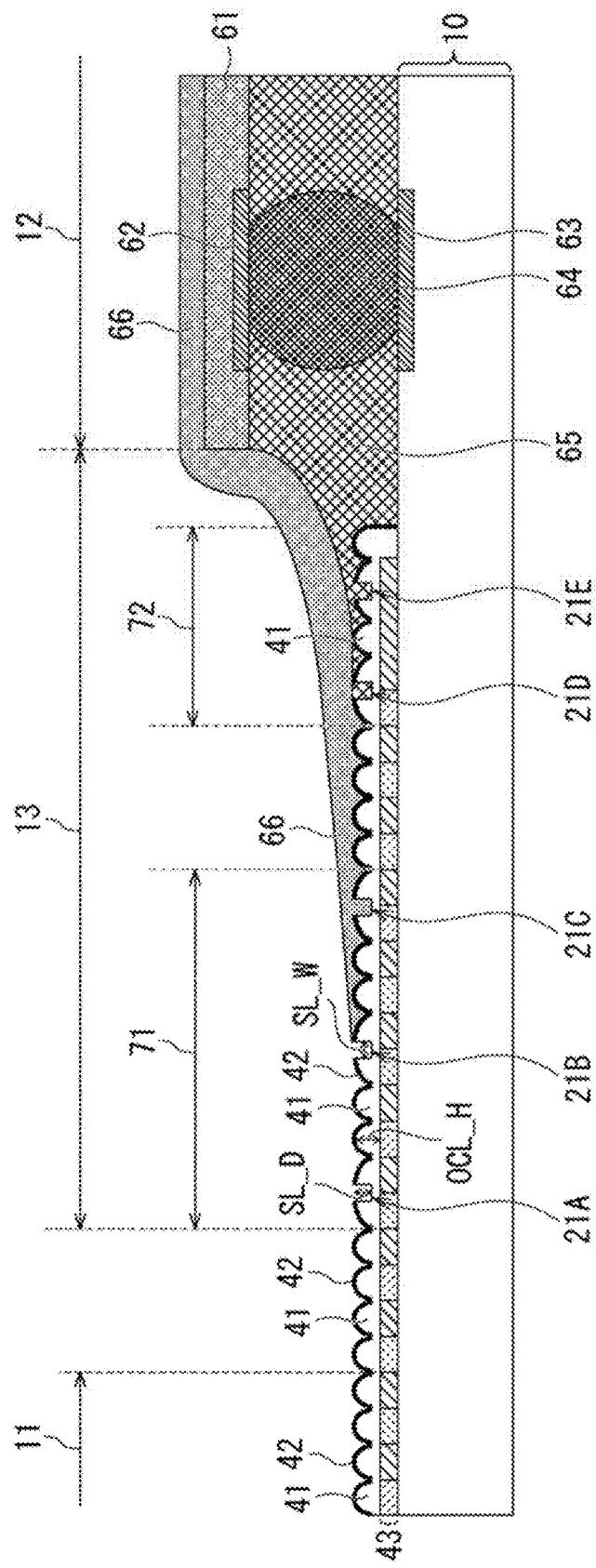
FIG. 6 is a cross-sectional view according to a variation example of the first embodiment.
Figure 7:
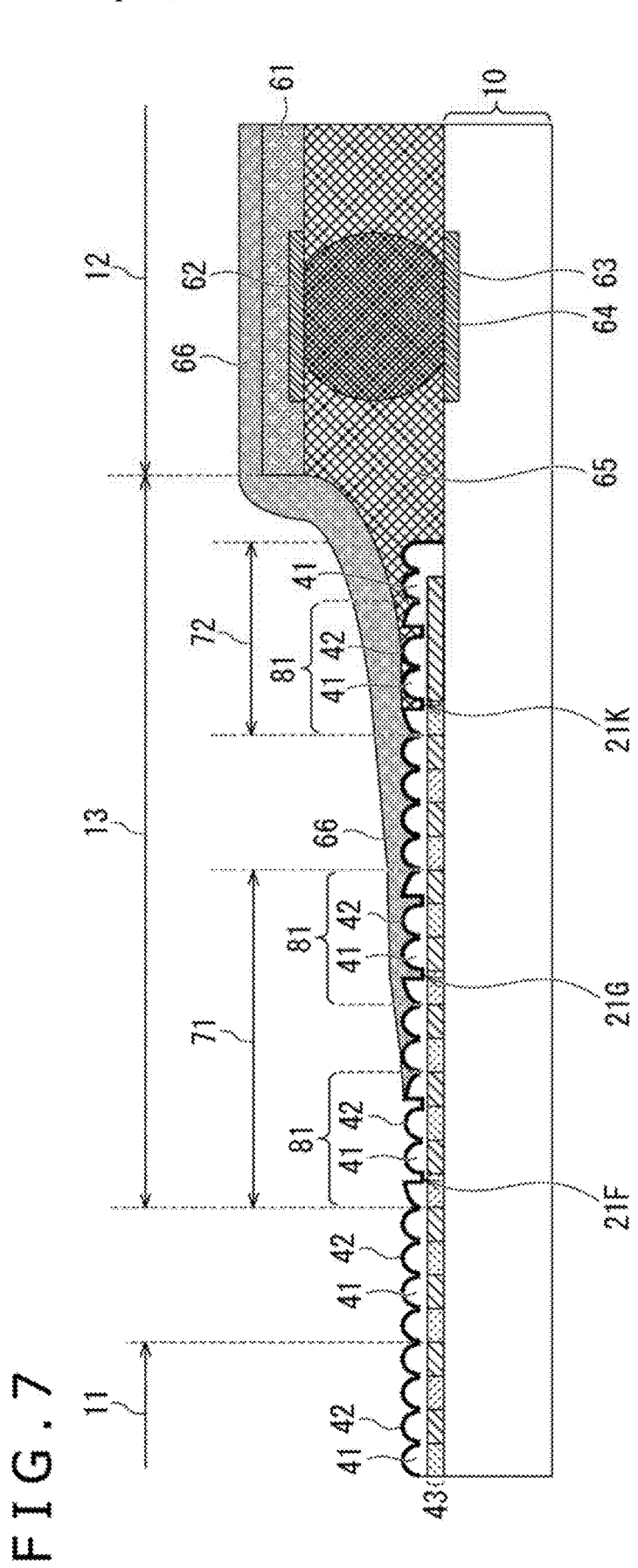
FIG. 7 is a cross-sectional view according to a variation example of the second embodiment.

FIG. 6 is a cross-sectional view depicting a variation example of the first embodiment, and FIG. 7 is a cross-sectional view depicting a variation example of the second embodiment.

In the variation examples depicted in FIGS. 6 and 7, a shape of an OCL in the UF dam area 72 is changed from that according to the first and the second embodiments.

Specifically, in the UF dam area 72 according to the first embodiment depicted in FIG. 2, two slits 21D and 21E are formed in a portion in which an OCL material is formed flatly. In the variation example depicted in FIG. 6, similarly to the light-shielding resin dam area 71, the OCL 41 is formed and two slits 21D and 21E are formed in portions in which a shape of OCLs each having a plane size that is an integral multiple of that of the OCL 41 are formed.

Further, in the variation example depicted in FIG. 7, similarly to the light-shielding resin dam area 71 according to the second embodiment, the slit area 81 in which a slit 21K is provided in the UF dam area 72. Further, the same OCL 41 as that in the pixel area 11 is formed as the low reflection projection on a bottom surface of the slit 21K.

As described above, a shape of the OCL material in which the slit 21 is formed in the UF dam area 72 may be adapted to the shape of the OCL in the light-shielding resin dam area 71.

<5. Manufacturing Method>

Figure 8:
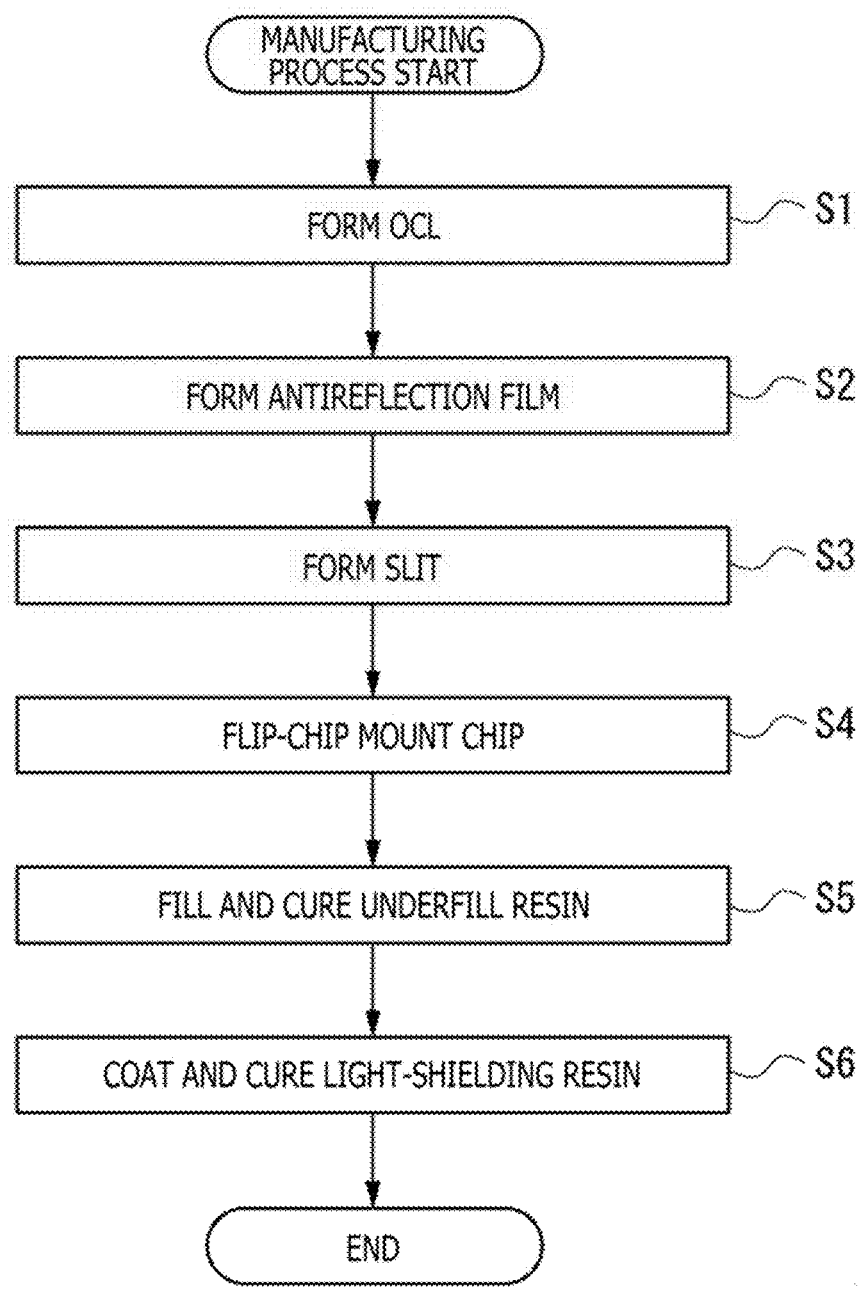
FIG. 8 is a flowchart describing a method for manufacturing a solid-state image pickup element.

A method for manufacturing the solid-state image pickup element 1 will be described with reference to FIG. 8.

On an upper surface of the light emitting surface side of the semiconductor substrate 10 in which photodiodes, a plurality of transistors, and the like are formed, the color filter layer 43 is formed. Then, in step S1, the OCLs 41 are formed on the color filter layer 43. The OCLs 41 are disposed in an extended manner from the pixel area 11 and are formed also in the dam area 13. Further, in the slit area 81 in which the slit 21 is formed in the dam area 13, an OCL having a size larger than a plane size of the OCL 41 is formed.

In step S2, over the upper surfaces of the OCLs 41 (also including the OCL in the slit area 81) in the pixel area 11 and the dam area 13, the antireflection films 42 are formed.

In step S3, the slit 21 is formed in the slit area 81 in the dam area 13. Note that, as described above, an order in which the slit 21 and the antireflection film 42 are formed may be reversed.

In step S4, the chip 61 is flip-chip mounted in the chip mounting area 12 of the semiconductor substrate 10.

In step S5, between the chip 61 in the chip mounting area 12 and the semiconductor substrate 10, the underfill resin 65 is filled and cured.

In step S6, in the area including the upper surface and side surfaces of the chip 61 and the upper surface of the underfill resin 65, the light-shielding resin 66 is coated and then cured.

As described above, the solid-state image pickup element 1 is manufactured.

<6. Application Example to Electronic Equipment>

The solid-state image pickup element 1 described above can be applied to various electronic equipment, for example, an image pickup apparatus such as a digital still camera or a digital video camera, a mobile phone having an image pickup function, or an audio player having an image pickup function.

Figure 9:
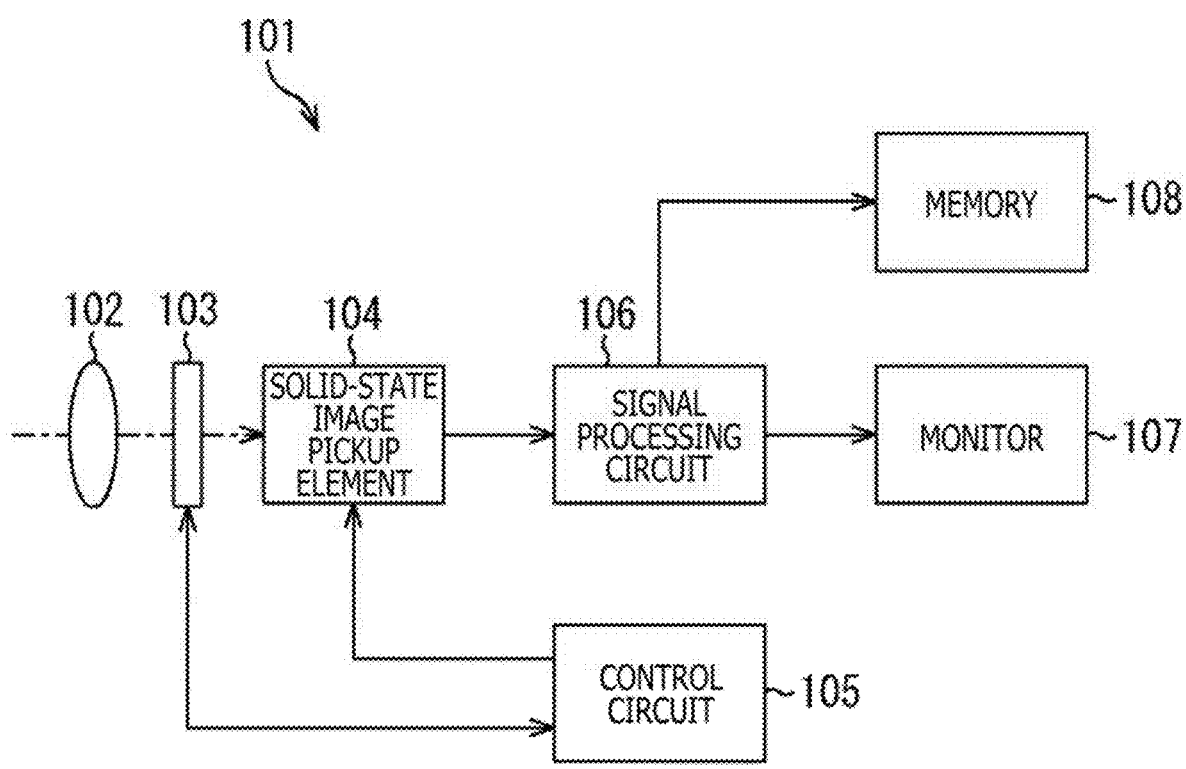
FIG. 9 is a block diagram depicting a configuration example of an image pickup apparatus functioning as electronic equipment to which the present technology is applied.

FIG. 9 is a block diagram depicting a configuration example of an image pickup apparatus functioning as electronic equipment to which the present technology is applied.

An image pickup apparatus 101 depicted in FIG. 9 includes an optical system 102, a shutter device 103, a solid-state image pickup element 104, a control circuit 105, a signal processing circuit 106, a monitor 107, and a memory 108 and can capture a still image and a moving image.

The optical system 102 includes one or a plurality of lenses, guides light (incident light) from a subject to the solid-state image pickup element 104, and forms an image on a light receiving surface of the solid-state image pickup element 104.

The shutter device 103 is arranged between the optical system 102 and the solid-state image pickup element 104. Further, the shutter device 103 controls a light irradiation period and a light-shielding period to the solid-state image pickup element 104 in accordance with control of the control circuit 105.

The solid-state image pickup element 104 includes the solid-state image pickup element 1 described above. The solid-state image pickup element 104 accumulates signal charges for a certain period in accordance with light forming an optical image on the light receiving surface via the optical system 102 and the shutter device 103. The signal charges accumulated in the solid-state image pickup element 104 are transferred in accordance with a drive signal (timing signal) supplied from the control circuit 105. The solid-state image pickup element 104 may be configured as one chip by itself. Alternatively, the solid-state image pickup element 104 may be configured as a part of a camera module packaged with the optical system 102, the signal processing circuit 106, or the like.

The control circuit 105 outputs a drive signal for controlling a transfer operation of the solid-state image pickup element 104 and a shutter operation of the shutter device 103, and drives the solid-state image pickup element 104 and the shutter device 103.

The signal processing circuit 106 performs various kinds of signal processing on a pixel signal output from the solid-state image pickup element 104. An image (image data) obtained by performing the signal processing by the signal processing circuit 106 is supplied to the monitor 107 to be displayed thereon or is supplied to the memory 108 to be stored (recorded) therein.

As described above, the solid-state image pickup element 1 according to each of the embodiments described above is used as the solid-state image pickup element 104, so that the capturing in which the flare characteristics are improved can be realized. Accordingly, the quality of captured images can also be increased in the image pickup apparatus 101, which is a video camera, a digital still camera, a cameral module for mobile devices such as mobile phones, or the like.

<7. Usage Example of Image Sensor>

Figure 10:
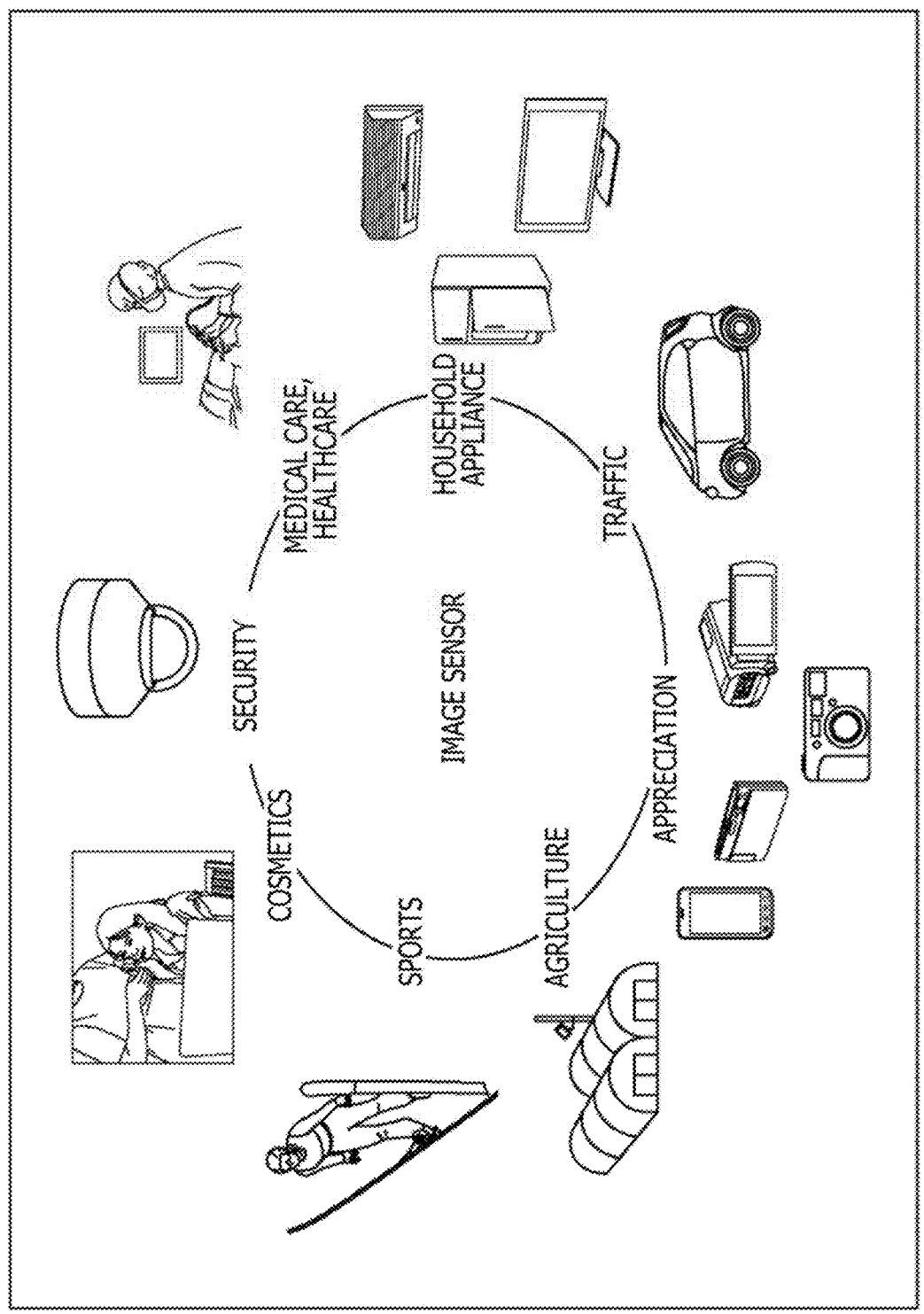
FIG. 10 is a diagram depicting a usage example of an image sensor.

FIG. 10 is a diagram depicting a usage example of an image sensor using the above-described solid-state image pickup element 1.

The image sensor using the above-described solid-state image pickup element 1 can be used, for example, in various cases in which light such as visible light, infrared light, ultraviolet light, or an X-ray is sensed, as described below.

An apparatus for photographing an image for use in appreciation such as a digital camera or a mobile device having a camera function An apparatus used for traffic such as a vehicle-mounted sensor that photographs a front, a rear, a circumference, or an inside etc. of a vehicle or a monitoring camera that monitors moving vehicles or roads, or a ranging sensor that measures a distance between vehicles for a safety drive of automatic stop etc. or recognition etc. of a state of a driver An apparatus for use in household appliances such as a TV set, a refrigerator, or an air conditioner in order to photograph a gesture of a user and perform an equipment operation in accordance with the gesture An apparatus for use in medical care or healthcare such as an endoscope or a device for imaging a blood vessel by reception of infrared light An apparatus for use in security such as a monitoring camera for security application or a camera for person authentication application An apparatus for cosmetic use such as a skin measuring instrument for photographing a skin or a microscope for photographing a scalp An apparatus for use in sport such as an action camera or a wearable camera for sport application etc.

An apparatus for use in agriculture such as a camera for monitoring a state of fields or crops <8. Application Example to In-Vivo Information Acquisition System>

The technology (the technology) according to the present disclosure can be applied to various products. For example, the technology according to the present disclosure may be applied to an in-vivo information acquisition system of a patient using a capsule type endoscope.

Figure 11:
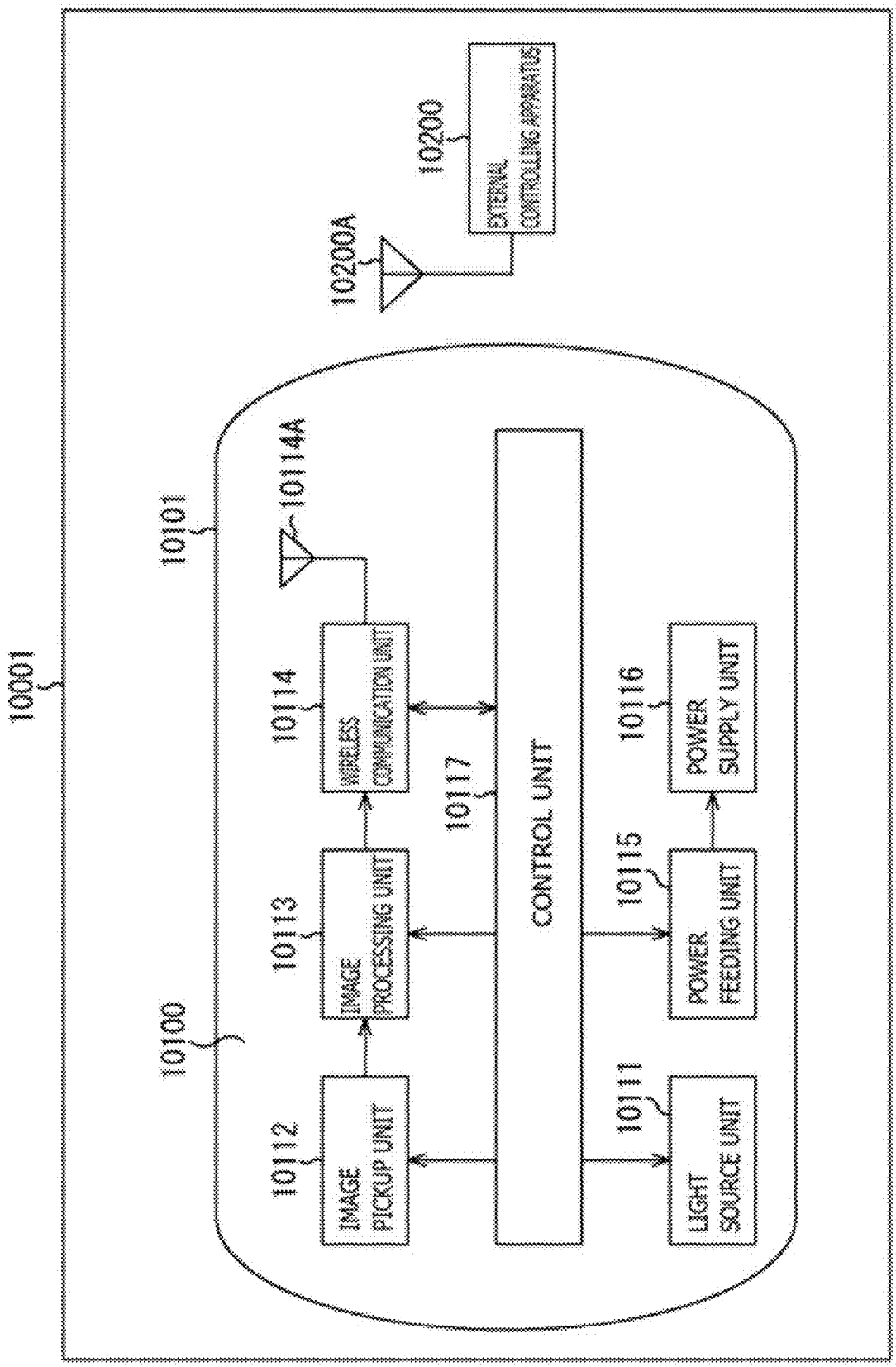
FIG. 11 is a block diagram depicting an example of a schematic configuration of an in-vivo information acquisition system.

FIG. 11 is a block diagram depicting an example of a schematic configuration of an in-vivo information acquisition system of a patient using a capsule type endoscope, to which the technology according to an embodiment of the present disclosure (present technology) can be applied.

The in-vivo information acquisition system 10001 includes a capsule type endoscope 10100 and an external controlling apparatus 10200.

The capsule type endoscope 10100 is swallowed by a patient at the time of inspection. The capsule type endoscope 10100 has an image pickup function and a wireless communication function and successively picks up an image of the inside of an organ such as the stomach or an intestine (hereinafter referred to as in-vivo image) at predetermined intervals while it moves inside of the organ by peristaltic motion for a period of time until it is naturally discharged from the patient. Then, the capsule type endoscope 10100 successively transmits information of the in-vivo image to the external controlling apparatus 10200 outside the body by wireless transmission.

The external controlling apparatus 10200 integrally controls operation of the in-vivo information acquisition system 10001. Further, the external controlling apparatus 10200 receives information of an in-vivo image transmitted thereto from the capsule type endoscope 10100 and generates image data for displaying the in-vivo image on a display apparatus (not depicted) on the basis of the received information of the in-vivo image.

In the in-vivo information acquisition system 10001, an in-vivo image imaged a state of the inside of the body of a patient can be acquired at any time in this manner for a period of time until the capsule type endoscope 10100 is discharged after it is swallowed.

A configuration and functions of the capsule type endoscope 10100 and the external controlling apparatus 10200 are described in more detail below.

The capsule type endoscope 10100 includes a housing 10101 of the capsule type, in which a light source unit 10111, an image pickup unit 10112, an image processing unit 10113, a wireless communication unit 10114, a power feeding unit 10115, a power supply unit 10116 and a control unit 10117 are accommodated.

The light source unit 10111 includes a light source such as, for example, a light emitting diode (LED) and irradiates light on an image pickup field-of-view of the image pickup unit 10112.

The image pickup unit 10112 includes an image pickup element and an optical system including a plurality of lenses provided at a preceding stage to the image pickup element. Reflected light (hereinafter referred to as observation light) of light irradiated on a body tissue which is an observation target is condensed by the optical system and introduced into the image pickup element. In the image pickup unit 10112, the incident observation light is photoelectrically converted by the image pickup element, by which an image signal corresponding to the observation light is generated. The image signal generated by the image pickup unit 10112 is provided to the image processing unit 10113.

The image processing unit 10113 includes a processor such as a central processing unit (CPU) or a graphics processing unit (GPU) and performs various signal processes for an image signal generated by the image pickup unit 10112. The image processing unit 10113 provides the image signal for which the signal processes have been performed thereby as RAW data to the wireless communication unit 10114.

The wireless communication unit 10114 performs a predetermined process such as a modulation process for the image signal for which the signal processes have been performed by the image processing unit 10113 and transmits the resulting image signal to the external controlling apparatus 10200 through an antenna 10114A. Further, the wireless communication unit 10114 receives a control signal relating to driving control of the capsule type endoscope 10100 from the external controlling apparatus 10200 through the antenna 10114A. The wireless communication unit 10114 provides the control signal received from the external controlling apparatus 10200 to the control unit 10117.

The power feeding unit 10115 includes an antenna coil for power reception, a power regeneration circuit for regenerating electric power from current generated in the antenna coil, a voltage booster circuit and so forth. The power feeding unit 10115 generates electric power using the principle of non-contact charging.

The power supply unit 10116 includes a secondary battery and stores electric power generated by the power feeding unit 10115. In FIG. 11, in order to avoid complicated illustration, an arrow mark indicative of a supply destination of electric power from the power supply unit 10116 and so forth are omitted. However, electric power stored in the power supply unit 10116 is supplied to and can be used to drive the light source unit 10111, the image pickup unit 10112, the image processing unit 10113, the wireless communication unit 10114 and the control unit 10117.

The control unit 10117 includes a processor such as a CPU and suitably controls driving of the light source unit 10111, the image pickup unit 10112, the image processing unit 10113, the wireless communication unit 10114 and the power feeding unit 10115 in accordance with a control signal transmitted thereto from the external controlling apparatus 10200.

The external controlling apparatus 10200 includes a processor such as a CPU or a GPU, a microcomputer, a control board or the like in which a processor and a storage element such as a memory are mixedly incorporated. The external controlling apparatus 10200 transmits a control signal to the control unit 10117 of the capsule type endoscope 10100 through an antenna 10200A to control operation of the capsule type endoscope 10100. In the capsule type endoscope 10100, an irradiation condition of light upon an observation target of the light source unit 10111 can be changed, for example, in accordance with a control signal from the external controlling apparatus 10200. Further, an image pickup condition (for example, a frame rate, an exposure value or the like of the image pickup unit 10112) can be changed in accordance with a control signal from the external controlling apparatus 10200. Further, the substance of processing by the image processing unit 10113 or a condition for transmitting an image signal from the wireless communication unit 10114 (for example, a transmission interval, a transmission image number or the like) may be changed in accordance with a control signal from the external controlling apparatus 10200.

Further, the external controlling apparatus 10200 performs various image processes for an image signal transmitted thereto from the capsule type endoscope 10100 to generate image data for displaying a picked up in-vivo image on the display apparatus. As the image processes, various signal processes can be performed such as, for example, a development process (demosaic process), an image quality improving process (bandwidth enhancement process, a super-resolution process, a noise reduction (NR) process and/or image stabilization process) and/or an enlargement process (electronic zooming process). The external controlling apparatus 10200 controls driving of the display apparatus to cause the display apparatus to display a picked up in-vivo image on the basis of generated image data. Alternatively, the external controlling apparatus 10200 may also control a recording apparatus (not depicted) to record generated image data or control a printing apparatus (not depicted) to output generated image data by printing.

In the above, an example of the in-vivo information acquisition system to which the technology according to the present disclosure can be applied has been described. The technology according to the present disclosure can be applied to the image pickup unit 10112 among the configurations described above. Specifically, the solid-state image pickup element 1 according to each embodiment described above can be applied to the image pickup unit 10112. The technology according to the present disclosure is applied to the image pickup unit 10112 to thereby provide the captured image in which the flare characteristics are improved. Therefore, a clearer image of a surgical region can be obtained and accuracy of the inspection is improved.

<9. Application Example to Endoscopic Surgery System>

The technology (the present technology) according to the present disclosure can be applied to various products. For example, the technology according to the present disclosure may be applied to the endoscopic surgery system.

Figure 12:
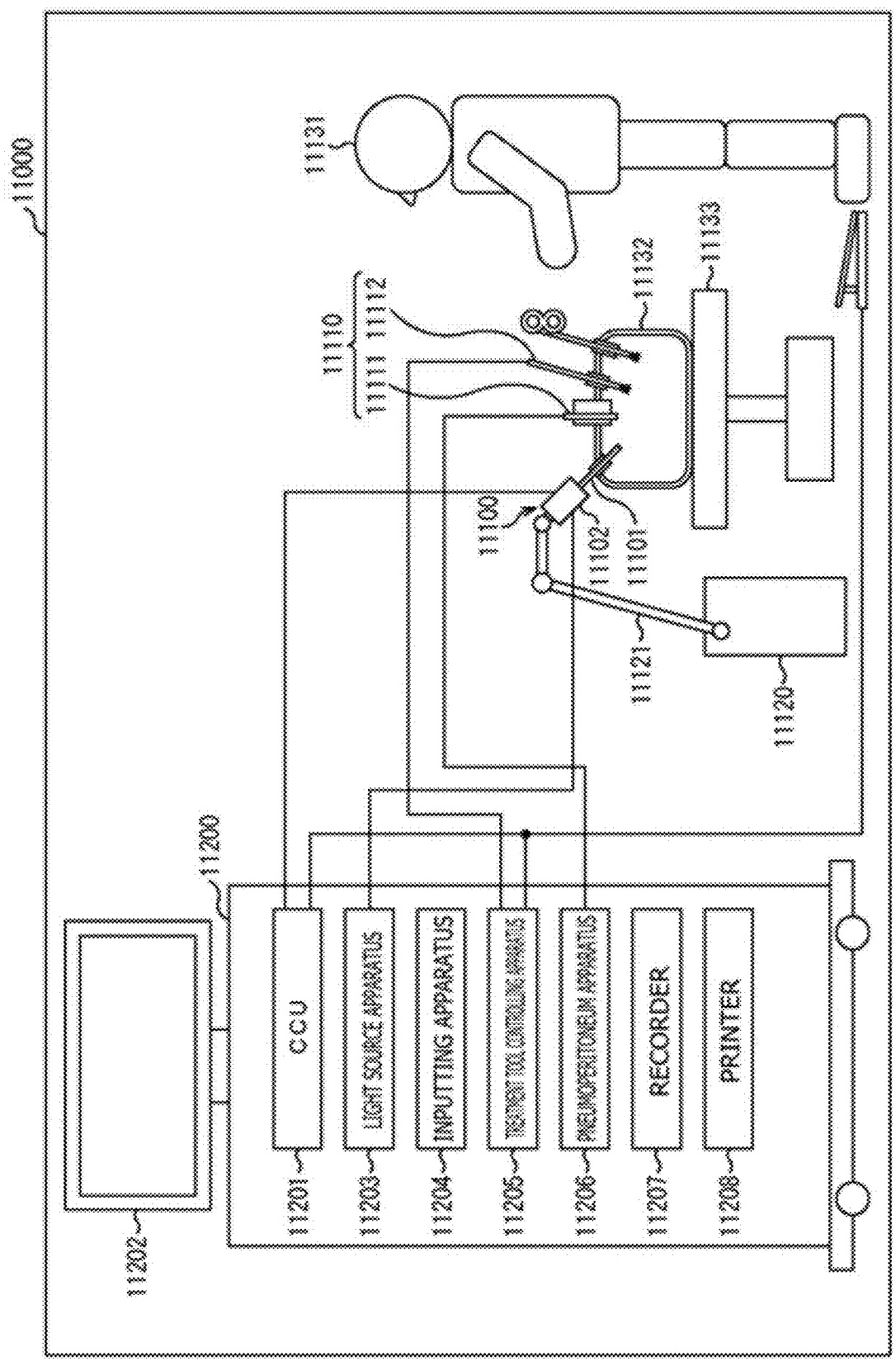
FIG. 12 is a view depicting an example of a schematic configuration of an endoscopic surgery system.

FIG. 12 is a view depicting an example of a schematic configuration of an endoscopic surgery system to which the technology according to an embodiment of the present disclosure (present technology) can be applied.

In FIG. 12, a state is illustrated in which a surgeon (medical doctor) 11131 is using an endoscopic surgery system 11000 to perform surgery for a patient 11132 on a patient bed 11133. As depicted, the endoscopic surgery system 11000 includes an endoscope 11100, other surgical tools 11110 such as a pneumoperitoneum tube 11111 and an energy device 11112, a supporting arm apparatus 11120 which supports the endoscope 11100 thereon, and a cart 11200 on which various apparatus for endoscopic surgery are mounted.

The endoscope 11100 includes a lens barrel 11101 having a region of a predetermined length from a distal end thereof to be inserted into a body cavity of the patient 11132, and a camera head 11102 connected to a proximal end of the lens barrel 11101. In the example depicted, the endoscope 11100 is depicted which includes as a rigid endoscope having the lens barrel 11101 of the hard type. However, the endoscope 11100 may otherwise be included as a flexible endoscope having the lens barrel 11101 of the flexible type.

The lens barrel 11101 has, at a distal end thereof, an opening in which an objective lens is fitted. A light source apparatus 11203 is connected to the endoscope 11100 such that light generated by the light source apparatus 11203 is introduced to a distal end of the lens barrel 11101 by a light guide extending in the inside of the lens barrel 11101 and is irradiated toward an observation target in a body cavity of the patient 11132 through the objective lens. It is to be noted that the endoscope 11100 may be a forward-viewing endoscope or may be an oblique-viewing endoscope or a side-viewing endoscope.

An optical system and an image pickup element are provided in the inside of the camera head 11102 such that reflected light (observation light) from the observation target is condensed on the image pickup element by the optical system. The observation light is photo-electrically converted by the image pickup element to generate an electric signal corresponding to the observation light, namely, an image signal corresponding to an observation image. The image signal is transmitted as RAW data to a CCU 11201.

The CCU 11201 includes a central processing unit (CPU), a graphics processing unit (GPU) or the like and integrally controls operation of the endoscope 11100 and a display apparatus 11202. Further, the CCU 11201 receives an image signal from the camera head 11102 and performs, for the image signal, various image processes for displaying an image based on the image signal such as, for example, a development process (demosaic process).

The display apparatus 11202 displays thereon an image based on an image signal, for which the image processes have been performed by the CCU 11201, under the control of the CCU 11201.

The light source apparatus 11203 includes a light source such as, for example, a light emitting diode (LED) and supplies irradiation light upon imaging of a surgical region to the endoscope 11100.

An inputting apparatus 11204 is an input interface for the endoscopic surgery system 11000. A user can perform inputting of various kinds of information or instruction inputting to the endoscopic surgery system 11000 through the inputting apparatus 11204. For example, the user would input an instruction or a like to change an image pickup condition (type of irradiation light, magnification, focal distance or the like) by the endoscope 11100.

A treatment tool controlling apparatus 11205 controls driving of the energy device 11112 for cautery or incision of a tissue, sealing of a blood vessel or the like. A pneumoperitoneum apparatus 11206 feeds gas into a body cavity of the patient 11132 through the pneumoperitoneum tube 11111 to inflate the body cavity in order to secure the field of view of the endoscope 11100 and secure the working space for the surgeon. A recorder 11207 is an apparatus capable of recording various kinds of information relating to surgery. A printer 11208 is an apparatus capable of printing various kinds of information relating to surgery in various forms such as a text, an image or a graph.

It is to be noted that the light source apparatus 11203 which supplies irradiation light when a surgical region is to be imaged to the endoscope 11100 may include a white light source which includes, for example, an LED, a laser light source or a combination of them. Where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 11203. Further, in this case, if laser beams from the respective RGB laser light sources are irradiated time-divisionally on an observation target and driving of the image pickup elements of the camera head 11102 are controlled in synchronism with the irradiation timings. Then images individually corresponding to the R, G and B colors can be also picked up time-divisionally. According to this method, a color image can be obtained even if color filters are not provided for the image pickup element.

Further, the light source apparatus 11203 may be controlled such that the intensity of light to be outputted is changed for each predetermined time. By controlling driving of the image pickup element of the camera head 11102 in synchronism with the timing of the change of the intensity of light to acquire images time-divisionally and synthesizing the images, an image of a high dynamic range free from underexposed blocked up shadows and overexposed highlights can be created.

Further, the light source apparatus 11203 may be configured to supply light of a predetermined wavelength band ready for special light observation. In special light observation, for example, by utilizing the wavelength dependency of absorption of light in a body tissue to irradiate light of a narrow band in comparison with irradiation light upon ordinary observation (namely, white light), narrow band observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation) or to obtain a fluorescent light image by locally injecting a reagent such as indocyanine green (ICG) into a body tissue and irradiating excitation light corresponding to a fluorescent light wavelength of the reagent upon the body tissue. The light source apparatus 11203 can be configured to supply such narrow-band light and/or excitation light suitable for special light observation as described above.

Figure 13:
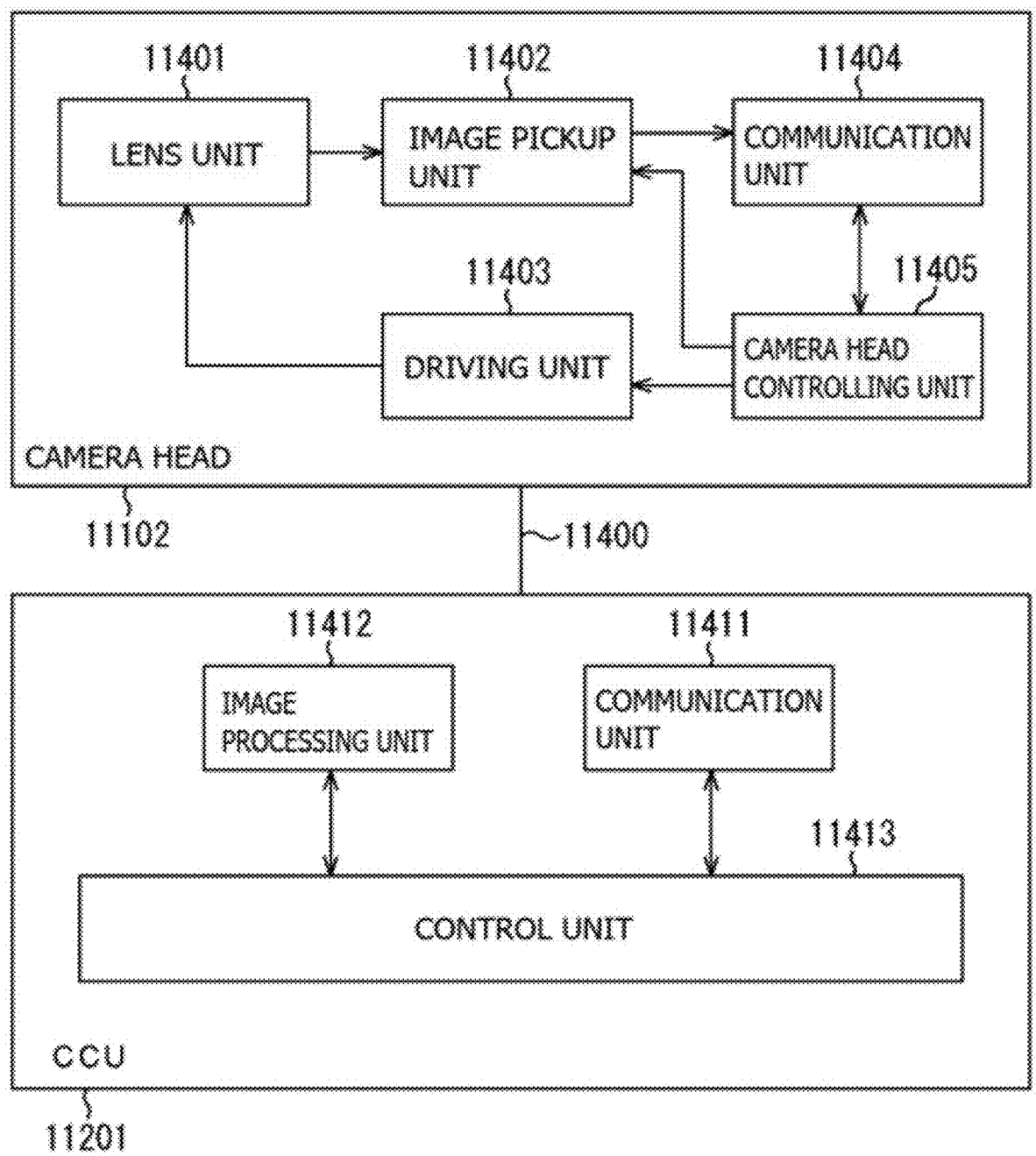
FIG. 13 is a block diagram depicting an example of a functional configuration of a camera head and a camera control unit (CCU).

FIG. 13 is a block diagram depicting an example of a functional configuration of the camera head 11102 and the CCU 11201 depicted in FIG. 12.

The camera head 11102 includes a lens unit 11401, an image pickup unit 11402, a driving unit 11403, a communication unit 11404 and a camera head controlling unit 11405. The CCU 11201 includes a communication unit 11411, an image processing unit 11412 and a control unit 11413. The camera head 11102 and the CCU 11201 are connected for communication to each other by a transmission cable 11400.

The lens unit 11401 is an optical system, provided at a connecting location to the lens barrel 11101. Observation light taken in from a distal end of the lens barrel 11101 is guided to the camera head 11102 and introduced into the lens unit 11401. The lens unit 11401 includes a combination of a plurality of lenses including a zoom lens and a focusing lens.

The number of image pickup elements which is included by the image pickup unit 11402 may be one (single-plate type) or a plural number (multi-plate type). Where the image pickup unit 11402 is configured as that of the multi-plate type, for example, image signals corresponding to respective R, G and B are generated by the image pickup elements, and the image signals may be synthesized to obtain a color image. The image pickup unit 11402 may also be configured so as to have a pair of image pickup elements for acquiring respective image signals for the right eye and the left eye ready for three dimensional (3D) display. If 3D display is performed, then the depth of a living body tissue in a surgical region can be comprehended more accurately by the surgeon 11131. It is to be noted that, where the image pickup unit 11402 is configured as that of stereoscopic type, a plurality of systems of lens units 11401 are provided corresponding to the individual image pickup elements.

Further, the image pickup unit 11402 may not necessarily be provided on the camera head 11102. For example, the image pickup unit 11402 may be provided immediately behind the objective lens in the inside of the lens barrel 11101.

The driving unit 11403 includes an actuator and moves the zoom lens and the focusing lens of the lens unit 11401 by a predetermined distance along an optical axis under the control of the camera head controlling unit 11405. Consequently, the magnification and the focal point of a picked up image by the image pickup unit 11402 can be adjusted suitably.

The communication unit 11404 includes a communication apparatus for transmitting and receiving various kinds of information to and from the CCU 11201. The communication unit 11404 transmits an image signal acquired from the image pickup unit 11402 as RAW data to the CCU 11201 through the transmission cable 11400.

In addition, the communication unit 11404 receives a control signal for controlling driving of the camera head 11102 from the CCU 11201 and supplies the control signal to the camera head controlling unit 11405. The control signal includes information relating to image pickup conditions such as, for example, information that a frame rate of a picked up image is designated, information that an exposure value upon image picking up is designated and/or information that a magnification and a focal point of a picked up image are designated.

It is to be noted that the image pickup conditions such as the frame rate, exposure value, magnification or focal point may be designated by the user or may be set automatically by the control unit 11413 of the CCU 11201 on the basis of an acquired image signal. In the latter case, an auto exposure (AE) function, an auto focus (AF) function and an auto white balance (AWB) function are incorporated in the endoscope 11100.

The camera head controlling unit 11405 controls driving of the camera head 11102 on the basis of a control signal from the CCU 11201 received through the communication unit 11404.

The communication unit 11411 includes a communication apparatus for transmitting and receiving various kinds of information to and from the camera head 11102. The communication unit 11411 receives an image signal transmitted thereto from the camera head 11102 through the transmission cable 11400.

Further, the communication unit 11411 transmits a control signal for controlling driving of the camera head 11102 to the camera head 11102. The image signal and the control signal can be transmitted by electrical communication, optical communication or the like.

The image processing unit 11412 performs various image processes for an image signal in the form of RAW data transmitted thereto from the camera head 11102.

The control unit 11413 performs various kinds of control relating to image picking up of a surgical region or the like by the endoscope 11100 and display of a picked up image obtained by image picking up of the surgical region or the like. For example, the control unit 11413 creates a control signal for controlling driving of the camera head 11102.

Further, the control unit 11413 controls, on the basis of an image signal for which image processes have been performed by the image processing unit 11412, the display apparatus 11202 to display a picked up image in which the surgical region or the like is imaged. Thereupon, the control unit 11413 may recognize various objects in the picked up image using various image recognition technologies. For example, the control unit 11413 can recognize a surgical tool such as forceps, a particular living body region, bleeding, mist when the energy device 11112 is used and so forth by detecting the shape, color and so forth of edges of objects included in a picked up image. The control unit 11413 may cause, when it controls the display apparatus 11202 to display a picked up image, various kinds of surgery supporting information to be displayed in an overlapping manner with an image of the surgical region using a result of the recognition. Where surgery supporting information is displayed in an overlapping manner and presented to the surgeon 11131, the burden on the surgeon 11131 can be reduced and the surgeon 11131 can proceed with the surgery with certainty.

The transmission cable 11400 which connects the camera head 11102 and the CCU 11201 to each other is an electric signal cable ready for communication of an electric signal, an optical fiber ready for optical communication or a composite cable ready for both of electrical and optical communications.

Here, while, in the example depicted, communication is performed by wired communication using the transmission cable 11400, the communication between the camera head 11102 and the CCU 11201 may be performed by wireless communication.

In the foregoing description, an example of the endoscopic surgery system to which the technology according to the present disclosure can be applied has been described. The technology according to the present disclosure can be applied to the image pickup unit 11402 of the camera head 11102 among the configurations described above. Specifically, the solid-state image pickup element 1 according to each embodiment described above can be applied to the image pickup unit 11402. The technology according to the present disclosure is applied to the image pickup unit 11402 to thereby provide the captured image in which the flare characteristics are improved. Therefore, a clearer image of a surgical region can be obtained.

Note that the endoscopic surgery system has been described herein by way of example, and further, the technology according to the present disclosure may be applied to other examples, for example, a microscopic surgery system and the like.

<10. Application Example to Mobile Body>

The technology (the present technology) according to the present disclosure can be applied to various products. For example, the technology according to the present disclosure may be realized as an apparatus mounted on any type of mobile body such as an automobile, an electric car, a hybrid electric car, a motorcycle, a bicycle, a personal mobility, an airplane, a drone, a ship, a robot, and the like.

Figure 14:
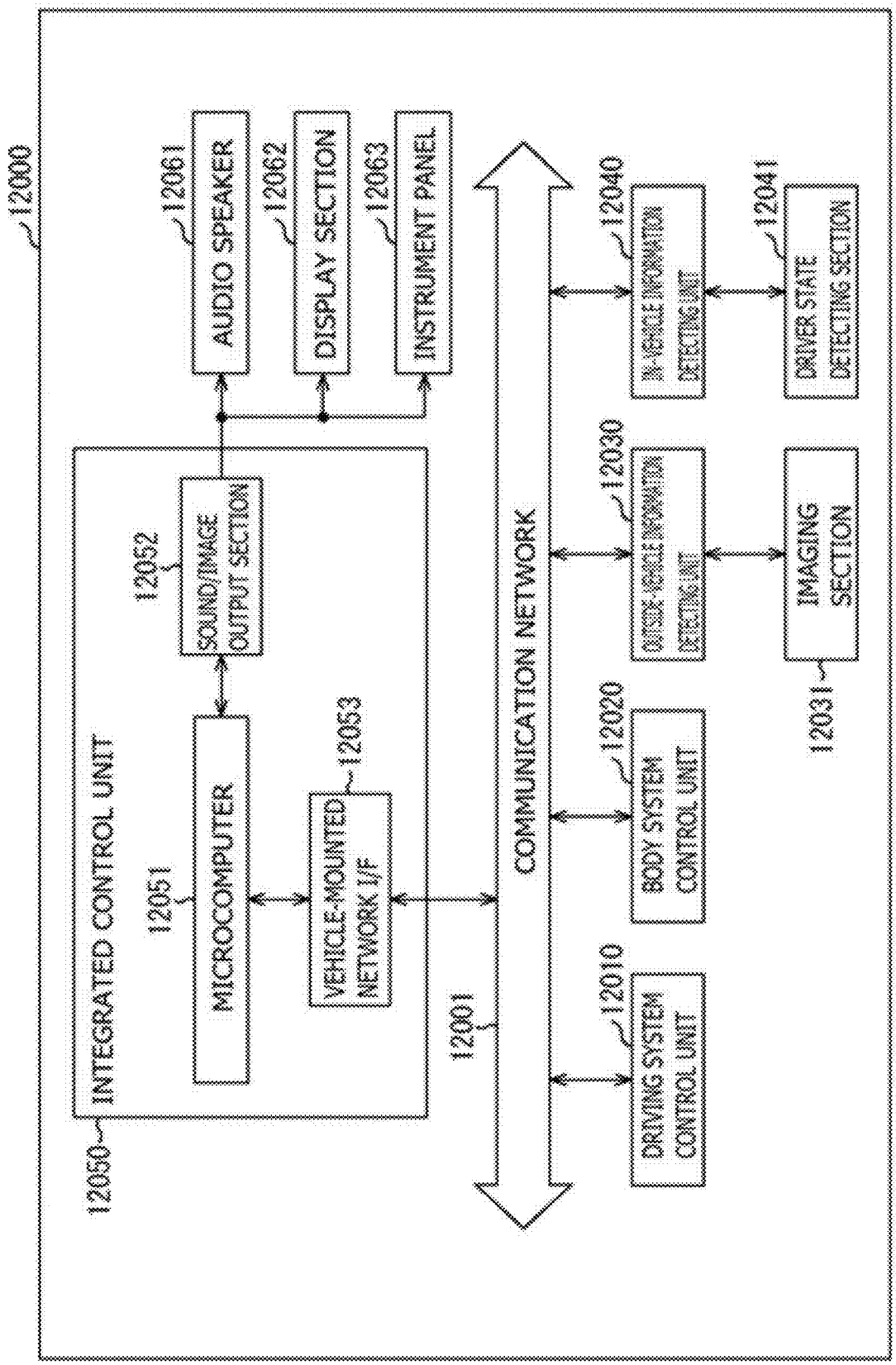
FIG. 14 is a block diagram depicting an example of a schematic configuration of a vehicle control system.

FIG. 14 is a block diagram depicting an example of schematic configuration of a vehicle control system as an example of a mobile body control system to which the technology according to an embodiment of the present disclosure can be applied.

The vehicle control system 12000 includes a plurality of electronic control units connected to each other via a communication network 12001. In the example depicted in FIG. 14, the vehicle control system 12000 includes a driving system control unit 12010, a body system control unit 12020, an outside-vehicle information detecting unit 12030, an in-vehicle information detecting unit 12040, and an integrated control unit 12050. In addition, a microcomputer 12051, a sound/image output section 12052, and a vehicle-mounted network interface (I/F) 12053 are illustrated as a functional configuration of the integrated control unit 12050.

The driving system control unit 12010 controls the operation of devices related to the driving system of the vehicle in accordance with various kinds of programs. For example, the driving system control unit 12010 functions as a control device for a driving force generating device for generating the driving force of the vehicle, such as an internal combustion engine, a driving motor, or the like, a driving force transmitting mechanism for transmitting the driving force to wheels, a steering mechanism for adjusting the steering angle of the vehicle, a braking device for generating the braking force of the vehicle, and the like.

The body system control unit 12020 controls the operation of various kinds of devices provided to a vehicle body in accordance with various kinds of programs. For example, the body system control unit 12020 functions as a control device for a keyless entry system, a smart key system, a power window device, or various kinds of lamps such as a headlamp, a backup lamp, a brake lamp, a turn signal, a fog lamp, or the like. In this case, radio waves transmitted from a mobile device as an alternative to a key or signals of various kinds of switches can be input to the body system control unit 12020. The body system control unit 12020 receives these input radio waves or signals, and controls a door lock device, the power window device, the lamps, or the like of the vehicle.

The outside-vehicle information detecting unit 12030 detects information about the outside of the vehicle including the vehicle control system 12000. For example, the outside-vehicle information detecting unit 12030 is connected with an imaging section 12031. The outside-vehicle information detecting unit 12030 makes the imaging section 12031 image an image of the outside of the vehicle, and receives the imaged image. On the basis of the received image, the outside-vehicle information detecting unit 12030 may perform processing of detecting an object such as a human, a vehicle, an obstacle, a sign, a character on a road surface, or the like, or processing of detecting a distance thereto.

The imaging section 12031 is an optical sensor that receives light, and which outputs an electric signal corresponding to a received light amount of the light. The imaging section 12031 can output the electric signal as an image, or can output the electric signal as information about a measured distance. In addition, the light received by the imaging section 12031 may be visible light, or may be invisible light such as infrared rays or the like.

The in-vehicle information detecting unit 12040 detects information about the inside of the vehicle. The in-vehicle information detecting unit 12040 is, for example, connected with a driver state detecting section 12041 that detects the state of a driver. The driver state detecting section 12041, for example, includes a camera that images the driver. On the basis of detection information input from the driver state detecting section 12041, the in-vehicle information detecting unit 12040 may calculate a degree of fatigue of the driver or a degree of concentration of the driver, or may determine whether the driver is dozing. [0132]

The microcomputer 12051 can calculate a control target value for the driving force generating device, the steering mechanism, or the braking device on the basis of the information about the inside or outside of the vehicle which information is obtained by the outside-vehicle information detecting unit 12030 or the in-vehicle information detecting unit 12040, and output a control command to the driving system control unit 12010. For example, the microcomputer 12051 can perform cooperative control intended to implement functions of an advanced driver assistance system (ADAS) which functions include collision avoidance or shock mitigation for the vehicle, following driving based on a following distance, vehicle speed maintaining driving, a warning of collision of the vehicle, a warning of deviation of the vehicle from a lane, or the like.

In addition, the microcomputer 12051 can perform cooperative control intended for automatic driving, which makes the vehicle to travel autonomously without depending on the operation of the driver, or the like, by controlling the driving force generating device, the steering mechanism, the braking device, or the like on the basis of the information about the outside or inside of the vehicle which information is obtained by the outside-vehicle information detecting unit 12030 or the in-vehicle information detecting unit 12040.

In addition, the microcomputer 12051 can output a control command to the body system control unit 12020 on the basis of the information about the outside of the vehicle which information is obtained by the outside-vehicle information detecting unit 12030. For example, the microcomputer 12051 can perform cooperative control intended to prevent a glare by controlling the headlamp so as to change from a high beam to a low beam, for example, in accordance with the position of a preceding vehicle or an oncoming vehicle detected by the outside-vehicle information detecting unit 12030.

The sound/image output section 12052 transmits an output signal of at least one of a sound and an image to an output device capable of visually or auditorily notifying information to an occupant of the vehicle or the outside of the vehicle. In the example of FIG. 14, an audio speaker 12061, a display section 12062, and an instrument panel 12063 are illustrated as the output device. The display section 12062 may, for example, include at least one of an on-board display and a head-up display.

Figure 15:
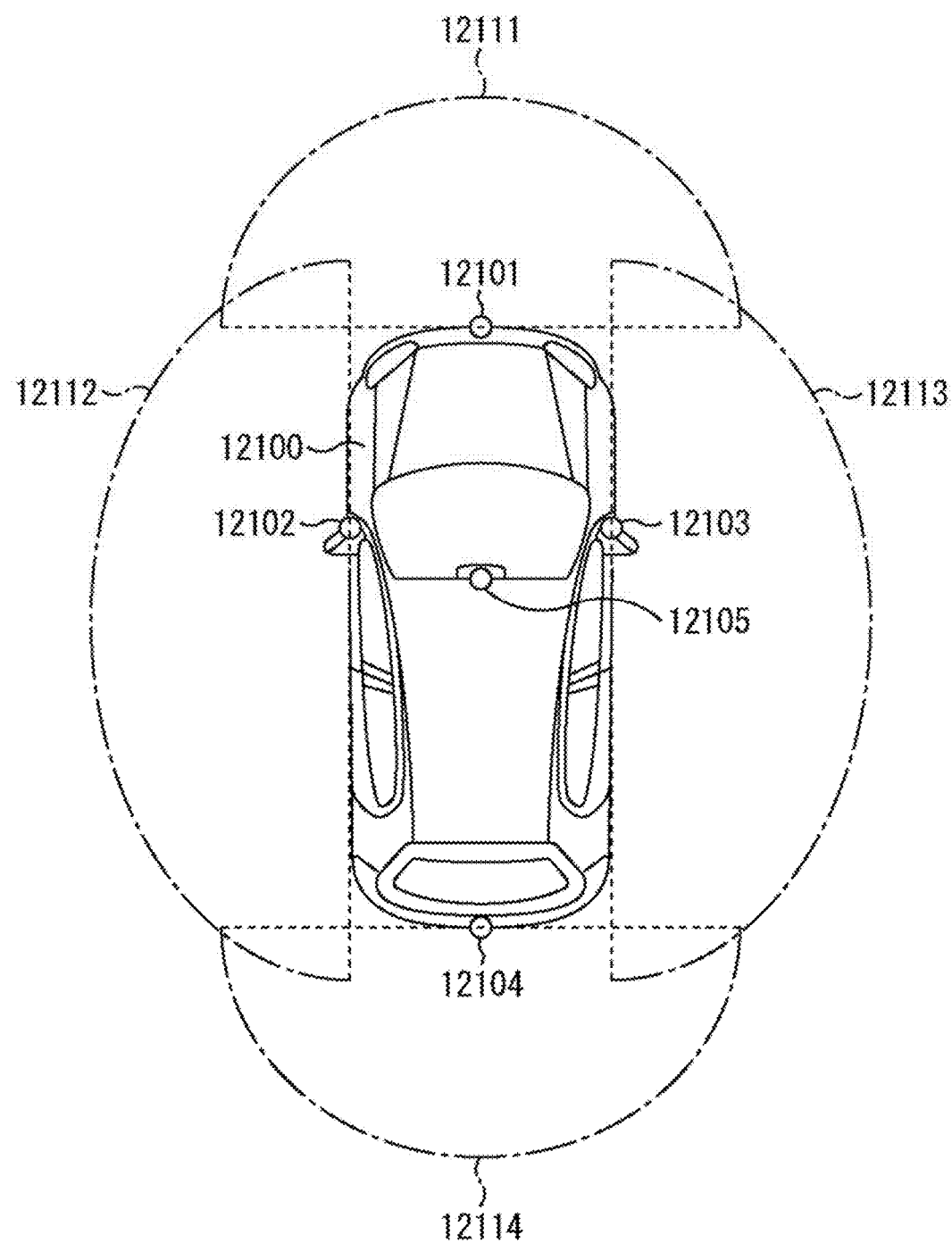
FIG. 15 is a diagram of assistance in explaining an example of installation positions of an outside-vehicle information detecting unit and an imaging section.

FIG. 15 is a diagram depicting an example of the installation position of the imaging section 12031.

In FIG. 15, the imaging section 12031 includes imaging sections 12101, 12102, 12103, 12104, and 12105.

The imaging sections 12101, 12102, 12103, 12104, and 12105 are, for example, disposed at positions on a front nose, sideview mirrors, a rear bumper, and a back door of the vehicle 12100 as well as a position on an upper portion of a windshield within the interior of the vehicle. The imaging section 12101 provided to the front nose and the imaging section 12105 provided to the upper portion of the windshield within the interior of the vehicle obtain mainly an image of the front of the vehicle 12100. The imaging sections 12102 and 12103 provided to the sideview mirrors obtain mainly an image of the sides of the vehicle 12100. The imaging section 12104 provided to the rear bumper or the back door obtains mainly an image of the rear of the vehicle 12100. The imaging section 12105 provided to the upper portion of the windshield within the interior of the vehicle is used mainly to detect a preceding vehicle, a pedestrian, an obstacle, a signal, a traffic sign, a lane, or the like.

Incidentally, FIG. 15 depicts an example of photographing ranges of the imaging sections 12101 to 12104. An imaging range 12111 represents the imaging range of the imaging section 12101 provided to the front nose. Imaging ranges 12112 and 12113 respectively represent the imaging ranges of the imaging sections 12102 and 12103 provided to the sideview mirrors. An imaging range 12114 represents the imaging range of the imaging section 12104 provided to the rear bumper or the back door. A bird's-eye image of the vehicle 12100 as viewed from above is obtained by superimposing image data imaged by the imaging sections 12101 to 12104, for example.

At least one of the imaging sections 12101 to 12104 may have a function of obtaining distance information. For example, at least one of the imaging sections 12101 to 12104 may be a stereo camera constituted of a plurality of imaging elements, or may be an imaging element having pixels for phase difference detection.

For example, the microcomputer 12051 can determine a distance to each three-dimensional object within the imaging ranges 12111 to 12114 and a temporal change in the distance (relative speed with respect to the vehicle 12100) on the basis of the distance information obtained from the imaging sections 12101 to 12104, and thereby extract, as a preceding vehicle, a nearest three-dimensional object in particular that is present on a traveling path of the vehicle 12100 and which travels in substantially the same direction as the vehicle 12100 at a predetermined speed (for example, equal to or more than 0 km/hour). Further, the microcomputer 12051 can set a following distance to be maintained in front of a preceding vehicle in advance, and perform automatic brake control (including following stop control), automatic acceleration control (including following start control), or the like. It is thus possible to perform cooperative control intended for automatic driving that makes the vehicle travel autonomously without depending on the operation of the driver or the like.

For example, the microcomputer 12051 can classify three-dimensional object data on three-dimensional objects into three-dimensional object data of a two-wheeled vehicle, a standard-sized vehicle, a large-sized vehicle, a pedestrian, a utility pole, and other three-dimensional objects on the basis of the distance information obtained from the imaging sections 12101 to 12104, extract the classified three-dimensional object data, and use the extracted three-dimensional object data for automatic avoidance of an obstacle. For example, the microcomputer 12051 identifies obstacles around the vehicle 12100 as obstacles that the driver of the vehicle 12100 can recognize visually and obstacles that are difficult for the driver of the vehicle 12100 to recognize visually. Then, the microcomputer 12051 determines a collision risk indicating a risk of collision with each obstacle. In a situation in which the collision risk is equal to or higher than a set value and there is thus a possibility of collision, the microcomputer 12051 outputs a warning to the driver via the audio speaker 12061 or the display section 12062, and performs forced deceleration or avoidance steering via the driving system control unit 12010. The microcomputer 12051 can thereby assist in driving to avoid collision.

At least one of the imaging sections 12101 to 12104 may be an infrared camera that detects infrared rays. The microcomputer 12051 can, for example, recognize a pedestrian by determining whether or not there is a pedestrian in imaged images of the imaging sections 12101 to 12104. Such recognition of a pedestrian is, for example, performed by a procedure of extracting characteristic points in the imaged images of the imaging sections 12101 to 12104 as infrared cameras and a procedure of determining whether or not it is the pedestrian by performing pattern matching processing on a series of characteristic points representing the contour of the object. When the microcomputer 12051 determines that there is a pedestrian in the imaged images of the imaging sections 12101 to 12104, and thus recognizes the pedestrian, the sound/image output section 12052 controls the display section 12062 so that a square contour line for emphasis is displayed so as to be superimposed on the recognized pedestrian. The sound/image output section 12052 may also control the display section 12062 so that an icon or the like representing the pedestrian is displayed at a desired position.

In the foregoing description, an example of the vehicle control system to which the technology according to the present disclosure can be applied has been described. The technology according to the present disclosure can be applied to the imaging section 12031 among the configurations described above. Specifically, the solid-state image pickup element 1 according to each embodiment described above can be applied to the imaging section 12031. The technology according to the present disclosure is applied to the imaging section 12031, and thereby the flare characteristics can be improved and a photographed image which allows a driver to easily view can be obtained. In addition, by using the obtained photographed image, fatigue of a driver can be relaxed, and a safety degree of a driver and a vehicle can be improved.

Further, the present technology is not limited to application to solid-state image pickup elements for detecting a distribution of incident amounts of visible light and capturing the detected distribution as an image. Further, the present technology can be applied to solid-state image pickup elements for capturing images representing distributions of incident amounts of an infrared ray, an X ray, or particles, etc., and a general solid-state image pickup element in a wider sense (physical quantity distribution detecting apparatus), such as a fingerprint detecting sensor, for detecting a distribution of other physical quantity such as a pressures and a static capacitance to capture the image thereof.

In addition, the present technology is not limited to solid-state image pickup elements but can be applied to a general semiconductor apparatus having other semiconductor integrated circuit. The semiconductor apparatus in this case includes an OCL area (corresponding to the pixel area 11 of the solid-state image pickup element 1) in which the OCLs 41 are formed in a matrix, the chip mounting area 12 in which the chip 61 is flip-chip mounted, and the dam area 13 that is disposed around the chip mounting area 12, and in the dam area 13, the same OCL as that in the OCL area is formed.

The embodiments of the present technology are not limited to the embodiments described above, but various changes are available within the scope without departing from the spirit of the present technology.

For example, a mode as an arbitrary combination of all or a part of a plurality of the embodiments described above may be employed.

Note that the effects disclosed in the present specification are illustrative only and not limitative, and thus there may be effects other than those disclosed in the present specification.

Note that the present technology may have the following configurations.

(1)

A solid-state image pickup element including:
a pixel area in which a plurality of pixels is two-dimensionally arranged in a matrix;
a chip mounting area in which a chip is flip-chip mounted; and
a dam area that is arranged around the chip mounting area and in which one or more slits that block an outflow of a resin are formed, in which
in the dam area, the same OCL as that in the pixel area is formed.

(2)

The solid-state image pickup element according to (1) above, further including:
a low reflection projection on a bottom surface of the slit.

(3)

The solid-state image pickup element according to (2) above, in which
the low reflection projection has a shape of a same OCL as that in the pixel area.

(4)

The solid-state image pickup element according to (2) above, in which
the low reflection projection has a shape of an OCL smaller than that in the pixel area.

(5)

The solid-state image pickup element according to (2) above, in which
the low reflection projection has a shape of an OCL different from that in the pixel area.

(6)

The solid-state image pickup element according to any one of (1) through (5) above, in which
a plane size of an OCL in which the slit is formed includes a size of an integral multiple of a plane size of the OCL in the pixel area.

(7)

The solid-state image pickup element according to any one of (1) through (6) above, in which
the slit includes a slit that blocks an outflow of a light-shielding resin that covers an upper surface and side surfaces of the chip.

(8)

The solid-state image pickup element according to any one of (1) through (6) above, in which
the slit includes a slit that blocks an outflow of an underfill resin that is filled in a range in which the chip is flip-chip mounted.

(9)

The solid-state image pickup element according to any one of (1) through (8) above, in which
an antireflection film is formed over an upper surface of an OCL in the dam area.

(10)

Electronic equipment including:
a solid-state image pickup element including
a pixel area in which a plurality of pixels is two-dimensionally arranged in a matrix,
a chip mounting area in which a chip is flip-chip mounted, and
a dam area that is arranged around the chip mounting area and in which one or more slits that block an outflow of a resin are formed,
in the dam area, the same OCL as that in the pixel area being formed.

(11)

A semiconductor apparatus including:
an OCL area in which an OCL is formed in a matrix;
a chip mounting area in which a chip is flip-chip mounted; and
a dam area that is arranged around the chip mounting area and in which one or more slits that block an outflow of a resin are formed, in which
in the dam area, the same OCL as that in the OCL area is formed.

REFERENCE SIGNS LIST

Solid-state image pickup element, 10 Semiconductor substrate, 11 Pixel area, 12 Chip mounting area, 13 Dam area, (21A to 21G) Slit, 22 Electrode pad, 41 OCL, 42 Antireflection film, 43 Color filter layer, 61 Chip, 64 Solder bump, 65 Underfill resin, 66 Light-shielding resin, 91 Low reflection projection, 101 Image pickup apparatus, 104 Solid-state image pickup element

The invention claimed is:

1. A solid-state image pickup element, comprising:
   a pixel area that comprises a plurality of pixels arranged two-dimensionally in a matrix;
   a chip mounting area that comprises a chip which is flip-chip mounted; and
   a dam area that, is around the chip mounting area, comprises at least one slit to block an outflow of a resin, wherein
   the dam area comprises a first on-chip lens (OCL), and
   the at least one slit is in the first OCL which is in the dam area.

2. The solid-state image pickup element according to claim 1, further comprising a low reflection projection on a bottom surface of the at least one slit.

3. The solid-state image pickup element according to claim 2, wherein the low reflection projection has a shape of a second OCL that is in the pixel area.

4. The solid-state image pickup element according to claim 2, wherein the low reflection projection has a shape of a third OCL smaller than a second OCL in the pixel area.

5. The solid-state image pickup element according to claim 2, wherein the low reflection projection has a shape of a third OCL different from a second OCL in the pixel area.

6. The solid-state image pickup element according to claim 1, wherein
   a size of the first OCL includes a size of an integral multiple of a size of a second OCL in the pixel area, and
   the size of the first OCL is viewed in a plan view with a direction of viewing normal to an active surface of the chip.

7. The solid-state image pickup element according to claim 1, wherein
   the at least one slit blocks an outflow of the resin that covers an upper surface and side surfaces of the chip, and
   the resin is a light-shielding resin.

8. The solid-state image pickup element according to claim 1, wherein
   the at least one slit blocks an outflow of the resin filled in a region in which the chip is flip-chip mounted, and
   the resin is an underfill resin.

9. The solid-state image pickup element according to claim 1, wherein an antireflection film is over an upper surface of the first OCL in the dam area.

10. An electronic, comprising:
    a solid-state image pickup element that comprises:
       a pixel area that comprises a plurality of pixels arranged two-dimensionally in a matrix,
       a chip mounting area that comprises a chip which is flip-chip mounted, and
       a dam area that, is around the chip mounting area, comprises at least one slit to block an outflow of a resin, wherein
       the dam area comprises an on-chip lens (OCL), and
       the at least one slit is in the OCL which is in the dam area.

11. A semiconductor apparatus, comprising:
    an on-chip lens (OCL) area that comprises a first OCL in a matrix;
    a chip mounting area that comprises a chip which is flip-chip mounted; and
    a dam area that, is around the chip mounting area, comprising at least one slit to block an outflow of a resin, wherein
    the dam area comprises a second OCL, and
    the at least one slit is in the second OCL which is in the dam area.

* * * * *